US012656351B2

(12) United States Patent
Schwaderer et al.

(10) Patent No.: US 12,656,351 B2
(45) Date of Patent: Jun. 16, 2026

(54) METHODS FOR IDENTIFYING AND TREATING URINARY TRACT INFECTIONS

(71) Applicants: THE TRUSTEES OF INDIANA UNIVERSITY, Bloomington, IN (US); THE RESEARCH INSTITUTE AT NATIONWIDE CHILDREN'S HOSPITAL, Columbus, IN (US)

(72) Inventors: Andrew L Schwaderer, Zionsville, IN (US); Dong Liang, Indianapolis, IN (US); David Hains, Indianapolis, IN (US); Joshua R. Watson, Columbus, IN (US)

(73) Assignees: THE TRUSTEES OF INDIANA UNIVERSITY, Bloomington, IN (US); THE RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 1144 days.

(21) Appl. No.: 17/631,899

(22) PCT Filed: Aug. 6, 2020

(86) PCT No.: PCT/US2020/045172
§ 371 (c)(1),
(2) Date: Feb. 1, 2022

(87) PCT Pub. No.: WO2021/026335
PCT Pub. Date: Feb. 11, 2021

(65) Prior Publication Data
US 2022/0334132 A1        Oct. 20, 2022

Related U.S. Application Data

(60) Provisional application No. 62/884,484, filed on Aug. 8, 2019.

(51) Int. Cl.
*G01N 33/68* (2006.01)
*C07K 16/24* (2006.01)

(52) U.S. Cl.
CPC ......... *G01N 33/6893* (2013.01); *C07K 16/24* (2013.01); *G01N 2800/348* (2013.01)

(58) Field of Classification Search
CPC ......... G01N 33/6893; G01N 2800/348; C07K 16/24
See application file for complete search history.

(56) References Cited

U.S. PATENT DOCUMENTS

2005/0176030 A1    8/2005  Gan et al.
2007/0099251 A1    5/2007  Zhang et al.
                   (Continued)

FOREIGN PATENT DOCUMENTS

EP          1522594 A2 *  4/2005  ........... C12Q 1/6886
WO    WO-2019122088 A1 *  6/2019  ........... G01N 33/502

OTHER PUBLICATIONS

Waikar SS, Sabbisetti VS, Bonventre JV. Normalization of urinary biomarkers to creatinine during changes in glomerular filtration rate. Kidney Int. Sep. 2010;78(5):486-94. doi: 10.1038/ki.2010.165. Epub Jun. 16, 2010. PMID: 20555318; PMCID: PMC3025699. (Year: 2010).*

(Continued)

*Primary Examiner* — Gregory S Emch
*Assistant Examiner* — Michael Cameron Sveiven
(74) *Attorney, Agent, or Firm* — Barnes & Thornburg LLP

(57) ABSTRACT

Compositions and methods are provided for the detection of a urinary tract infection by detecting and quantitating at least eight proteins in the sample. Aptamer based proteomic analysis revealed a urine protein signature that differentiated urinary tract infections from culture negative urine samples, (Continued)

B-cell lymphoma 6 protein

| Results | |
| --- | --- |
| Area | 0.9102 |
| Std. Error | 0.05613 |
| 95% confidence interval | 0.8002 to 1.02 |
| P value | <0.0001 |

C-X-C motif chemokine 6

| Results | |
| --- | --- |
| Area | 0.9492 |
| Std. Error | 0.03707 |
| 95% confidence interval | 0.8766 to 1.022 |
| P value | <0.0001 | regardless of pyuria status. Inclusion of these candidate biomarkers, either alone or in combination, to traditional urinalysis biomarkers assist clinicians in identifying true urinary tract infections, from culture negative pyuria, at the point of care The identified patients can then be treated with a therapeutic pharmaceutical composition comprising standard antibiotics.

7 Claims, 12 Drawing Sheets

Specification includes a Sequence Listing.

(56) References Cited

U.S. PATENT DOCUMENTS

| | | | |
|---|---|---|---|
| 2007/0166699 | A1 | 7/2007 | Zwerschke et al. |
| 2007/0275003 | A1 | 11/2007 | Cassetti et al. |
| 2010/0041564 | A1 | 2/2010 | Russwurm et al. |
| 2010/0086942 | A1 | 4/2010 | Barker et al. |
| 2010/0190656 | A1 | 7/2010 | Li et al. |
| 2011/0124009 | A1 | 5/2011 | Wata et al. |
| 2011/0158952 | A1 | 6/2011 | Beach et al. |
| 2011/0183866 | A1 | 7/2011 | Clarke et al. |
| 2011/0287037 | A1 | 11/2011 | Gentschev et al. |
| 2013/0178377 | A1 | 7/2013 | Pieper et al. |
| 2015/0148254 | A1 | 5/2015 | Rimsza et al. |
| 2018/0224466 | A1 | 8/2018 | McPherson et al. |

OTHER PUBLICATIONS

PCT International Search Report and Written Opinion completed by the ISA/US on Nov. 1, 2020 and issued in connection with PCT/US2020/045172.

Forster et al. "Predictive ability of NGAL in identifying urinary tract infection in children with neurogenic bladders," Pediatric Nephrology, Mar. 12, 2018 (Mar. 12, 2018), vol. 33, No. 8, pp. 1365-1374.

* cited by examiner

C-X-C motif chemokine 13

Cathepsin S

| Results | |
|---|---|
| Area | 0.9063 |
| Std. Error | 0.05006 |
| 95% confidence interval.............0.8081 to 1.004 | |
| P value | <0.0001 |

| Results | |
|---|---|
| Area | 0.9336 |
| Std. Error | 0.04123 |
| 95% confidence interval.............0.8528 to 1.014 | |
| P value | <0.0001 |

Heat shock 70 kDa protein 1A

| Results | |
|---|---|
| Area | 0.9063 |
| Std. Error | 0.05284 |
| 95% confidence interval..............0.8027 to 1.01 | |
| P value | <0.0001 |

Mitogen-activated protein kinase 9

| Results | |
|---|---|
| Area | 0.9453 |
| Std. Error | 0.03924 |
| 95% confidence interval.............0.8684 to 1.022 | |
| P value | <0.0001 |

Protein E7_HPV18

|  | Results |  |
|---|---|---|
| Area |  | 0.9375 |
| Std. Error |  | 0.04212 |
| 95% confidence interval | | 0.855 to 1.02 |
| P value |  | <0.0001 |

Transgelin-2

|  | Results |  |
|---|---|---|
| Area |  | 0.9023 |
| Std. Error |  | 0.05609 |
| 95% confidence interval | | 0.7924 to 1.012 |
| P value |  | <0.0001 |

| Threshold | Sensitivity% | 95% C | Specificity% | 95% C | LR |
|---|---|---|---|---|---|
| 40.45 | 87.5 | 61.65% to 98.45% | 93.75 | 69.77% to 99.84% | 14 |

| Threshold | Sensitivity% | 95% C | Specificity% | 95% C | LR |
|---|---|---|---|---|---|
| 2.862 | 81.25 | 53.35 to 95.95% | 93.75 | 69.77% to 99.84% | 13 |

| Threshold | Sensitivity% | 95% C | Specificity% | 95% C | LR |
|---|---|---|---|---|---|
| 1.201 | 68.75 | 41.34% to 88.98% | 93.75 | 69.77% to 99.84% | 11 |

| Threshold | Sensitivity% | 95% C | Specificity% | 95% C | LR |
|---|---|---|---|---|---|
| 5.295 | 81.25 | 54.35% to 95.95% | 93.75 | 69.77% to 99.84% | 13 |

Heat shock 70 kDa protein 1A

| Threshold | Sensitivity% | 95% C | Specificity% | 95% C | LR |
|---|---|---|---|---|---|
| 7.694 | 56.25 | 29.88% to 80.25% | 93.75 | 69.77% to 99.84% | 9 |

Mitogen activated protein kinase 9

| Threshold | Sensitivity% | 95% C | Specificity% | 95% C | LR |
|---|---|---|---|---|---|
| 15.8 | 87.5 | 61.65% to 98.45% | 93.75 | 69.77% to 99.84% | 14 |

| Threshold | Sensitivity% | 95% C | Specificity% | 95% C | LR |
|---|---|---|---|---|---|
| 7.444 | 87.5 | 61.65% to 98.45% | 93.75 | 69.77% to 99.84% | 14 |

| Threshold | Sensitivity% | 95% C | Specificity% | 95% C | LR |
|---|---|---|---|---|---|
| 84.13 | 75 | 47.62% to 92.73% | 87.5 | 61.65% to 98.45% | 6 |

Fold change between UTI and non-UTI

SEQUENCE LISTING

<160> NUMBER OF SEQ ID NOS: 31

<210> SEQ ID NO 1
<211> LENGTH: 17
<212> TYPE: DNA
<213> ORGANISM: Homo sapiens

-continued

<400> SEQUENCE: 1
actgaacagt caccgac                                                    17

<210> SEQ ID NO 2
<211> LENGTH: 20
<212> TYPE: DNA
<213> ORGANISM: Homo sapiens

<400> SEQUENCE: 2
aaacattgtg acttggctac                                                 20

<210> SEQ ID NO 3
<211> LENGTH: 20
<212> TYPE: DNA
<213> ORGANISM: Homo sapiens

<400> SEQUENCE: 3
attgtgagaa gtgtaacctg                                                 20

<210> SEQ ID NO 4
<211> LENGTH: 21
<212> TYPE: DNA
<213> ORGANISM: Homo sapiens

<400> SEQUENCE: 4
tttgggtaga ttctgagaag g                                               21

<210> SEQ ID NO 5
<211> LENGTH: 21
<212> TYPE: DNA
<213> ORGANISM: Homo sapiens

<400> SEQUENCE: 5
atgctagaac agtgacaaat c                                               21

<210> SEQ ID NO 6
<211> LENGTH: 20
<212> TYPE: DNA
<213> ORGANISM: Homo sapiens

<400> SEQUENCE: 6
tcttctgttc ctataagggc                                                 20

<210> SEQ ID NO 7
<211> LENGTH: 20
<212> TYPE: DNA
<213> ORGANISM: Homo sapiens

<400> SEQUENCE: 7
aatttcctgt gtttgcaatg                                                 20

<210> SEQ ID NO 8
<211> LENGTH: 20
<212> TYPE: DNA
<213> ORGANISM: Homo sapiens

<400> SEQUENCE: 8
aaaatggcct gagttaagtg                                                 20

<210> SEQ ID NO 9
<211> LENGTH: 20
<212> TYPE: DNA

<213> ORGANISM: Homo sapiens

<400> SEQUENCE: 9
tcagatgcag cagtaagtag                                            20

<210> SEQ ID NO 10
<211> LENGTH: 20
<212> TYPE: DNA
<213> ORGANISM: Homo sapiens

<400> SEQUENCE: 10
aggtgagagt tccttcaatg                                            20

<210> SEQ ID NO 11
<211> LENGTH: 20
<212> TYPE: DNA
<213> ORGANISM: Homo sapiens

<400> SEQUENCE: 11
tctacagaag tggtgtctac                                            20

<210> SEQ ID NO 12
<211> LENGTH: 20
<212> TYPE: DNA
<213> ORGANISM: Homo sapiens

<400> SEQUENCE: 12
cctttatttc ttgccatccg                                            20

<210> SEQ ID NO 13
<211> LENGTH: 20
<212> TYPE: DNA
<213> ORGANISM: Homo sapiens

<400> SEQUENCE: 13
aaagggaata agtactgggc                                            20

<210> SEQ ID NO 14
<211> LENGTH: 21
<212> TYPE: DNA
<213> ORGANISM: Homo sapiens

<400> SEQUENCE: 14
cagtgttttc ctcagaaaga g                                          21

<210> SEQ ID NO 15
<211> LENGTH: 22
<212> TYPE: DNA
<213> ORGANISM: Homo sapiens

<400> SEQUENCE: 15
catagtctgg aagaagaaca ag                                         22

<210> SEQ ID NO 16
<211> LENGTH: 20
<212> TYPE: DNA
<213> ORGANISM: Homo sapiens

<400> SEQUENCE: 16
aagaatgcag gtgttcttag                                            20

<210> SEQ ID NO 17
<211> LENGTH: 20

-continued

```
<212> TYPE: DNA
<213> ORGANISM: Homo sapiens

<400> SEQUENCE: 17
cactgacatc ttccaaactg                                          20

<210> SEQ ID NO 18
<211> LENGTH: 20
<212> TYPE: DNA
<213> ORGANISM: Homo sapiens

<400> SEQUENCE: 18
ccttggattt cttagggaac                                          20

<210> SEQ ID NO 19
<211> LENGTH: 18
<212> TYPE: DNA
<213> ORGANISM: Homo sapiens

<400> SEQUENCE: 19
tgcatggacc taaggcaa                                            18

<210> SEQ ID NO 20
<211> LENGTH: 16
<212> TYPE: DNA
<213> ORGANISM: Homo sapiens

<400> SEQUENCE: 20
gctgggatgc acacca                                              16

<210> SEQ ID NO 21
<211> LENGTH: 19
<212> TYPE: DNA
<213> ORGANISM: Homo sapiens

<400> SEQUENCE: 21
tttccttgac tcggaaatg                                           19

<210> SEQ ID NO 22
<211> LENGTH: 18
<212> TYPE: DNA
<213> ORGANISM: Homo sapiens

<400> SEQUENCE: 22
tccgaatagt tgcccttg                                            18

<210> SEQ ID NO 23
<211> LENGTH: 706
<212> TYPE: PRT
<213> ORGANISM: Homo sapiens

<400> SEQUENCE: 23

Met Ala Ser Pro Ala Asp Ser Cys Ile Gln Phe Thr Arg His Ala Ser
1               5                   10                  15

Asp Val Leu Leu Asn Leu Asn Arg Leu Arg Ser Arg Asp Ile Leu Thr
            20                  25                  30

Asp Val Val Ile Val Val Ser Arg Glu Gln Phe Arg Ala His Lys Thr
        35                  40                  45

Val Leu Met Ala Cys Ser Gly Leu Phe Tyr Ser Ile Phe Thr Asp Gln
    50                  55                  60

Leu Lys Cys Asn Leu Ser Val Ile Asn Leu Asp Pro Glu Ile Asn Pro
65                  70                  75                  80
```

```
Glu Gly Phe Cys Ile Leu Leu Asp Phe Met Tyr Thr Ser Arg Leu Asn
              85                  90                  95

Leu Arg Glu Gly Asn Ile Met Ala Val Met Ala Thr Ala Met Tyr Leu
            100                 105                 110

Gln Met Glu His Val Val Asp Thr Cys Arg Lys Phe Ile Lys Ala Ser
            115                 120                 125

Glu Ala Glu Met Val Ser Ala Ile Lys Pro Pro Arg Glu Glu Phe Leu
        130                 135                 140

Asn Ser Arg Met Leu Met Pro Gln Asp Ile Met Ala Tyr Arg Gly Arg
145                 150                 155                 160

Glu Val Val Glu Asn Asn Leu Pro Leu Arg Ser Ala Pro Gly Cys Glu
                165                 170                 175

Ser Arg Ala Phe Ala Pro Ser Leu Tyr Ser Gly Leu Ser Thr Pro Pro
            180                 185                 190

Ala Ser Tyr Ser Met Tyr Ser His Leu Pro Val Ser Ser Leu Leu Phe
            195                 200                 205

Ser Asp Glu Glu Phe Arg Asp Val Arg Met Pro Val Ala Asn Pro Phe
        210                 215                 220

Pro Lys Glu Arg Ala Leu Pro Cys Asp Ser Ala Arg Pro Val Pro Gly
225                 230                 235                 240

Glu Tyr Ser Arg Pro Thr Leu Glu Val Ser Pro Asn Val Cys His Ser
            245                 250                 255

Asn Ile Tyr Ser Pro Lys Glu Thr Ile Pro Glu Glu Ala Arg Ser Asp
            260                 265                 270

Met His Tyr Ser Val Ala Glu Gly Leu Lys Pro Ala Ala Pro Ser Ala
            275                 280                 285

Arg Asn Ala Pro Tyr Phe Pro Cys Asp Lys Ala Ser Lys Glu Glu Glu
        290                 295                 300

Arg Pro Ser Ser Glu Asp Glu Ile Ala Leu His Phe Glu Pro Pro Asn
305                 310                 315                 320

Ala Pro Leu Asn Arg Lys Gly Leu Val Ser Pro Gln Ser Pro Gln Lys
            325                 330                 335

Ser Asp Cys Gln Pro Asn Ser Pro Thr Glu Ser Cys Ser Ser Lys Asn
            340                 345                 350

Ala Cys Ile Leu Gln Ala Ser Gly Ser Pro Pro Ala Lys Ser Pro Thr
            355                 360                 365

Asp Pro Lys Ala Cys Asn Trp Lys Lys Tyr Lys Phe Ile Val Leu Asn
        370                 375                 380

Ser Leu Asn Gln Asn Ala Lys Pro Glu Gly Pro Glu Gln Ala Glu Leu
385                 390                 395                 400

Gly Arg Leu Ser Pro Arg Ala Tyr Thr Ala Pro Pro Ala Cys Gln Pro
            405                 410                 415

Pro Met Glu Pro Glu Asn Leu Asp Leu Gln Ser Pro Thr Lys Leu Ser
            420                 425                 430

Ala Ser Gly Glu Asp Ser Thr Ile Pro Gln Ala Ser Arg Leu Asn Asn
            435                 440                 445

Ile Val Asn Arg Ser Met Thr Gly Ser Pro Arg Ser Ser Ser Glu Ser
        450                 455                 460

His Ser Pro Leu Tyr Met His Pro Pro Lys Cys Thr Ser Cys Gly Ser
465                 470                 475                 480

Gln Ser Pro Gln His Ala Glu Met Cys Leu His Thr Ala Gly Pro Thr
            485                 490                 495
```

-continued

```
Phe Pro Glu Glu Met Gly Glu Thr Gln Ser Glu Tyr Ser Asp Ser Ser
            500                 505                 510

Cys Glu Asn Gly Ala Phe Phe Cys Asn Glu Cys Asp Cys Arg Phe Ser
            515                 520                 525

Glu Glu Ala Ser Leu Lys Arg His Thr Leu Gln Thr His Ser Asp Lys
            530                 535                 540

Pro Tyr Lys Cys Asp Arg Cys Gln Ala Ser Phe Arg Tyr Lys Gly Asn
545                 550                 555                 560

Leu Ala Ser His Lys Thr Val His Thr Gly Glu Lys Pro Tyr Arg Cys
                565                 570                 575

Asn Ile Cys Gly Ala Gln Phe Asn Arg Pro Ala Asn Leu Lys Thr His
            580                 585                 590

Thr Arg Ile His Ser Gly Glu Lys Pro Tyr Lys Cys Glu Thr Cys Gly
            595                 600                 605

Ala Arg Phe Val Gln Val Ala His Leu Arg Ala His Val Leu Ile His
            610                 615                 620

Thr Gly Glu Lys Pro Tyr Pro Cys Glu Ile Cys Gly Thr Arg Phe Arg
625                 630                 635                 640

His Leu Gln Thr Leu Lys Ser His Leu Arg Ile His Thr Gly Glu Lys
                645                 650                 655

Pro Tyr His Cys Glu Lys Cys Asn Leu His Phe Arg His Lys Ser Gln
                660                 665                 670

Leu Arg Leu His Leu Arg Gln Lys His Gly Ala Ile Thr Asn Thr Lys
                675                 680                 685

Val Gln Tyr Arg Val Ser Ala Thr Asp Leu Pro Pro Glu Leu Pro Lys
            690                 695                 700

Ala Cys
705
```

<210> SEQ ID NO 24
<211> LENGTH: 331
<212> TYPE: PRT
<213> ORGANISM: Homo sapiens

<400> SEQUENCE: 24

```
Met Lys Arg Leu Val Cys Val Leu Leu Val Cys Ser Ser Ala Val Ala
1               5                   10                  15

Gln Leu His Lys Asp Pro Thr Leu Asp His His Trp His Leu Trp Lys
            20                  25                  30

Lys Thr Tyr Gly Lys Gln Tyr Lys Glu Lys Asn Glu Glu Ala Val Arg
            35                  40                  45

Arg Leu Ile Trp Glu Lys Asn Leu Lys Phe Val Met Leu His Asn Leu
        50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Ser Gln Trp Gln Arg Asn Ile Thr Tyr Lys Ser Asn Pro Asn
            100                 105                 110

Arg Ile Leu Pro Asp Ser Val Asp Trp Arg Glu Lys Gly Cys Val Thr
            115                 120                 125

Glu Val Lys Tyr Gln Gly Ser Cys Gly Ala Cys Trp Ala Phe Ser Ala
            130                 135                 140

Val Gly Ala Leu Glu Ala Gln Leu Lys Leu Lys Thr Gly Lys Leu Val
145                 150                 155                 160
```

```
Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
                180                 185                 190

Ile Asp Asn Lys Gly Ile Asp Ser Asp Ala Ser Tyr Pro Tyr Lys Ala
                195                 200                 205

Met Asp Gln Lys Cys Gln Tyr Asp Ser Lys Tyr Arg Ala Ala Thr Cys
        210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
                260                 265                 270

Thr Gln Asn Val Asn His Gly Val Leu Val Val Gly Tyr Gly Asp Leu
        275                 280                 285

Asn Gly Lys Glu Tyr Trp Leu Val Lys Asn Ser Trp Gly His Asn Phe
        290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330

<210> SEQ ID NO 25
<211> LENGTH: 424
<212> TYPE: PRT
<213> ORGANISM: Homo sapiens

<400> SEQUENCE: 25

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
                20                  25                  30

Gly Ser Gly Ala Gln Gly Ile Val Cys Ala Ala Phe Asp Thr Val Leu
        35                  40                  45

Gly Ile Asn Val Ala Val Lys Lys Leu Ser Arg Pro Phe Gln Asn Gln
        50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
                100                 105                 110

Ala Asn Leu Cys Gln Val Ile His Met Glu Leu Asp His Glu Arg Met
        115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
```

-continued

```
                195                 200                 205

Trp Ser Val Gly Cys Ile Met Gly Glu Leu Val Lys Gly Cys Val Ile
    210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
                260                 265                 270

Glu Leu Phe Pro Asp Trp Ile Phe Pro Ser Glu Ser Glu Arg Asp Lys
                275                 280                 285

Ile Lys Thr Ser Gln Ala Arg Asp Leu Leu Ser Lys Met Leu Val Ile
                290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
                340                 345                 350

Lys Glu Leu Ile Tyr Lys Glu Val Met Asp Trp Glu Glu Arg Ser Lys
                355                 360                 365

Asn Gly Val Val Lys Asp Gln Pro Ser Asp Ala Ala Val Ser Ser Asn
    370                 375                 380

Ala Thr Pro Ser Gln Ser Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
                420

<210> SEQ ID NO 26
<211> LENGTH: 641
<212> TYPE: PRT
<213> ORGANISM: Homo sapiens

<400> SEQUENCE: 26

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
                100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Ile
    130                 135                 140
```

```
Thr Val Pro Ala Tyr Phe Asn Asp Ser Gln Arg Gln Ala Thr Lys Asp
145             150                 155                 160

Ala Gly Val Ile Ala Gly Leu Asn Val Leu Arg Ile Ile Asn Glu Pro
                165                 170                 175

Thr Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
            325                 330                 335

Val Gly Gly Ser Thr Arg Ile Pro Lys Val Gln Lys Leu Leu Gln Asp
        340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
            405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
            485                 490                 495

Lys Ala Asn Lys Ile Thr Ile Thr Asn Asp Lys Gly Arg Leu Ser Lys
        500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
```

```
                    565              570              575
Val Ile Ser Trp Leu Asp Ala Asn Thr Leu Ala Glu Lys Asp Glu Phe
            580              585              590

Glu His Lys Arg Lys Glu Leu Glu Gln Val Cys Asn Pro Ile Ile Ser
        595              600              605

Gly Leu Tyr Gln Gly Ala Gly Gly Pro Gly Pro Gly Gly Phe Gly Ala
    610              615              620

Gln Gly Pro Lys Gly Gly Ser Gly Ser Gly Pro Thr Ile Glu Glu Val
625              630              635              640

Asp

<210> SEQ ID NO 27
<211> LENGTH: 469
<212> TYPE: PRT
<213> ORGANISM: Homo sapiens

<400> SEQUENCE: 27

Met His Ser Phe Pro Pro Leu Leu Leu Leu Phe Trp Gly Val Val
1               5              10              15

Ser His Ser Phe Pro Ala Thr Leu Glu Thr Gln Glu Gln Asp Val Asp
            20              25              30

Leu Val Gln Lys Tyr Leu Glu Lys Tyr Tyr Asn Leu Lys Asn Asp Gly
        35              40              45

Arg Gln Val Glu Lys Arg Arg Asn Ser Gly Pro Val Val Glu Lys Leu
    50              55              60

Lys Gln Met Gln Glu Phe Phe Gly Leu Lys Val Thr Gly Lys Pro Asp
65              70              75              80

Ala Glu Thr Leu Lys Val Met Lys Gln Pro Arg Cys Gly Val Pro Asp
            85              90              95

Val Ala Gln Phe Val Leu Thr Glu Gly Asn Pro Arg Trp Glu Gln Thr
        100              105              110

His Leu Thr Tyr Arg Ile Glu Asn Tyr Thr Pro Asp Leu Pro Arg Ala
        115              120              125

Asp Val Asp His Ala Ile Glu Lys Ala Phe Gln Leu Trp Ser Asn Val
    130              135              140

Thr Pro Leu Thr Phe Thr Lys Val Ser Glu Gly Gln Ala Asp Ile Met
145              150              155              160

Ile Ser Phe Val Arg Gly Asp His Arg Asp Asn Ser Pro Phe Asp Gly
            165              170              175

Pro Gly Gly Asn Leu Ala His Ala Phe Gln Pro Gly Pro Gly Ile Gly
            180              185              190

Gly Asp Ala His Phe Asp Glu Asp Glu Arg Trp Thr Asn Asn Phe Arg
        195              200              205

Glu Tyr Asn Leu His Arg Val Ala Ala His Glu Leu Gly His Ser Leu
    210              215              220

Gly Leu Ser His Ser Thr Asp Ile Gly Ala Leu Met Tyr Pro Ser Tyr
225              230              235              240

Thr Phe Ser Gly Asp Val Gln Leu Ala Gln Asp Asp Ile Asp Gly Ile
            245              250              255

Gln Ala Ile Tyr Gly Arg Ser Gln Asn Pro Val Gln Pro Ile Gly Pro
            260              265              270

Gln Thr Pro Lys Ala Cys Asp Ser Lys Leu Thr Phe Asp Ala Ile Thr
        275              280              285

Thr Ile Arg Gly Glu Val Met Phe Phe Lys Asp Arg Phe Tyr Met Arg
```

-continued

```
        290              295              300

Thr Asn Pro Phe Tyr Pro Glu Val Glu Leu Asn Phe Ile Ser Val Phe
305              310              315              320

Trp Pro Gln Leu Pro Asn Gly Leu Glu Ala Ala Tyr Glu Phe Ala Asp
             325              330              335

Arg Asp Glu Val Arg Phe Phe Lys Gly Asn Lys Tyr Trp Ala Val Gln
             340              345              350

Gly Gln Asn Val Leu His Gly Tyr Pro Lys Asp Ile Tyr Ser Ser Phe
             355              360              365

Gly Phe Pro Arg Thr Val Lys His Ile Asp Ala Ala Leu Ser Glu Glu
             370              375              380

Asn Thr Gly Lys Thr Tyr Phe Phe Val Ala Asn Lys Tyr Trp Arg Tyr
385              390              395              400

Asp Glu Tyr Lys Arg Ser Met Asp Pro Gly Tyr Pro Lys Met Ile Ala
             405              410              415

His Asp Phe Pro Gly Ile Gly His Lys Val Asp Ala Val Phe Met Lys
             420              425              430

Asp Gly Phe Phe Tyr Phe Phe His Gly Thr Arg Gln Tyr Lys Phe Asp
             435              440              445

Pro Lys Thr Lys Arg Ile Leu Thr Leu Gln Lys Ala Asn Ser Trp Phe
             450              455              460

Asn Cys Arg Lys Asn
465

<210> SEQ ID NO 28
<211> LENGTH: 107
<212> TYPE: PRT
<213> ORGANISM: Homo sapiens

<400> SEQUENCE: 28

Met Ala Arg Ala Ala Leu Ser Ala Ala Pro Ser Asn Pro Arg Leu Leu
1               5               10               15

Arg Val Ala Leu Leu Leu Leu Leu Leu Val Ala Ala Gly Arg Arg Ala
             20               25               30

Ala Gly Ala Ser Val Ala Thr Glu Leu Arg Cys Gln Cys Leu Gln Thr
             35               40               45

Leu Gln Gly Ile His Pro Lys Asn Ile Gln Ser Val Asn Val Lys Ser
             50               55               60

Pro Gly Pro His Cys Ala Gln Thr Glu Val Ile Ala Thr Leu Lys Asn
65               70               75               80

Gly Arg Lys Ala Cys Leu Asn Pro Ala Ser Pro Ile Val Lys Lys Ile
             85               90               95

Ile Glu Lys Met Leu Asn Ser Asp Lys Ser Asn
             100              105

<210> SEQ ID NO 29
<211> LENGTH: 109
<212> TYPE: PRT
<213> ORGANISM: Homo sapiens

<400> SEQUENCE: 29

Met Lys Phe Ile Ser Thr Ser Leu Leu Leu Met Leu Leu Val Ser Ser
1               5               10               15

Leu Ser Pro Val Gln Gly Val Leu Glu Val Tyr Tyr Thr Ser Leu Arg
             20               25               30

Cys Arg Cys Val Gln Glu Ser Ser Val Phe Ile Pro Arg Arg Phe Ile
```

```
          35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

<210> SEQ ID NO 30
<211> LENGTH: 105
<212> TYPE: PRT
<213> ORGANISM: Homo sapiens

<400> SEQUENCE: 30

Met His Gly Pro Lys Ala Thr Leu Gln Asp Ile Val Leu His Leu Glu
1                   5                   10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 31
<211> LENGTH: 199
<212> TYPE: PRT
<213> ORGANISM: Homo sapiens

<400> SEQUENCE: 31

Met Ala Asn Arg Gly Pro Ala Tyr Gly Leu Ser Arg Glu Val Gln Gln
1                   5                   10                  15

Lys Ile Glu Lys Gln Tyr Asp Ala Asp Leu Glu Gln Ile Leu Ile Gln
                20                  25                  30

Trp Ile Thr Thr Gln Cys Arg Lys Asp Val Gly Arg Pro Gln Pro Gly
            35                  40                  45

Arg Glu Asn Phe Gln Asn Trp Leu Lys Asp Gly Thr Val Leu Cys Glu
    50                  55                  60

Leu Ile Asn Ala Leu Tyr Pro Glu Gly Gln Ala Pro Val Lys Lys Ile
65                  70                  75                  80

Gln Ala Ser Thr Met Ala Phe Lys Gln Met Glu Gln Ile Ser Gln Phe
                85                  90                  95

Leu Gln Ala Ala Glu Arg Tyr Gly Ile Asn Thr Thr Asp Ile Phe Gln
            100                 105                 110

Thr Val Asp Leu Trp Glu Gly Lys Asn Met Ala Cys Val Gln Arg Thr
            115                 120                 125

Leu Met Asn Leu Gly Gly Leu Ala Val Ala Arg Asp Asp Gly Leu Phe
    130                 135                 140

Ser Gly Asp Pro Asn Trp Phe Pro Lys Lys Ser Lys Glu Asn Pro Arg
```

-continued

```
145              150              155              160

Asn Phe Ser Asp Asn Gln Leu Gln Glu Gly Lys Asn Val Ile Gly Leu
             165              170              175

Gln Met Gly Thr Asn Arg Gly Ala Ser Gln Ala Gly Met Thr Gly Tyr
             180              185              190

Gly Met Pro Arg Gln Ile Leu
             195
```

METHODS FOR IDENTIFYING AND TREATING URINARY TRACT INFECTIONS

CROSS REFERENCE TO RELATED APPLICATIONS

This application is a U.S. national counterpart application of international application serial No. PCT/US2020/045172 filed Aug. 6, 2020, which claims priority U.S. Provisional Patent Application No. 62/884,484 filed on Aug. 8, 2019, the disclosures of which are hereby expressly incorporated by reference in their entireties.

STATEMENT OF GOVERNMENT SUPPORT

This invention was made with government support under DK114035 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 30 kilobytes ACII (Text) file named "321431_ST25.txt," created on Jul. 24, 2020.

BACKGROUND OF THE DISCLOSURE

Urinary tract infections (UTI) are frequently encountered in both adults and children. They account for about 7% of pediatric emergency department antibiotic prescriptions, following acute respiratory tract infections as the leading indication. They account for seven million physician office visits, and 400,000 hospitalizations annually in the United States, an increase of 52% between 1998-2011 at a cost of about 2.8 billion dollars. Diagnosis of UTI is typically at point-of-care by patient symptoms and by clinical urinalysis identification of nitrites and leukocyte esterase (LE) using test-strips (also termed dipsticks), with confirmation by urine culture growth of ≥50,000 colony forming bacterial units. However, diagnosis of urinary tract infections by urinalysis has limitations, as does urine culture. Accurate results can depend on collection methods. Test strips incorporate assays for leukocyte esterase, a nonspecific marker for pyuria, and nitrites, a bacterial product. The sensitivity and specificity for leukocyte esterase in a test strip assay to detect childhood urinary tract infections is 83% and 78%, respectively. The sensitivity and specificity for nitrites in a test strip assay to detect childhood urinary tract infections is 53% and 98% respectively. Urine cultures can take 24-72 hours to complete. Patients are at risk for being prescribed antibiotics, or are delayed treatment with risk for UTI progression. Antibiotic resistance among uropathogens is also increasing.

In children, pyuria is defined by 5 white blood cells (WBC) per high power field (hpf), ≥10 WBC per cubic millimeter ($mm^3$), or ≥1+LE on urinalysis. A condition historically termed "sterile pyuria", and now termed "culture negative pyuria" because urine is recognized to contain viable microbiota, and which is defined as the presence of leukocyte esterase and/or white blood cells but with no growth upon urine culture, can be caused by infectious conditions such as renal tuberculosis, herpes simplex virus, chlamydia, or by non-infectious inflammatory conditions such as Kawasaki disease, foreign bodies, and interstitial nephritis.

Initiating antibiotic treatment in a patient with a suspected UTI, but later confirmed to be culture negative pyuria, exposes that patient to unneeded antibiotics, and potentially increases the risk of antibiotic-resistant bacteria. Conversely, waiting for culture results to initiate antibiotic treatment in a patient with a bona fide UTI risks a more complicated UTI, for example, a progression from cystitis to pyelonephritis or even urosepsis. Accordingly, methods that increase the accuracy of diagnosing UTI are needed.

Analysis of human urine is the first known type of laboratory medicine, dating back to 4,000 BCE. Hippocrates associated increasing urine sediment with increasing fevers; if the aforementioned urine sediment was due to white blood cells, this association would be the earliest known description of a UTI biomarker. Urine test strips have been used since they were developed in the 1950s-1960s in point of care diagnosis of UTIs. However, urinalysis has limitations regarding sensitivity and specificity; its key UTI diagnostic components detects white blood cells in the urine, but this finding is not necessarily specific to UTI. Despite the need for more judicious use of antibiotics secondary to increasing rates of antibiotic resistant bacteria, point of care diagnosis of UTIs has remained largely unchanged since the introduction of urine test strips. One strategy is to detect bacterial products such as bacterial nuclease activity, but identifying the bacterial load indicative of a UTI may be problematic because urine contains a microbiota. Increased urine levels of innate immune proteins in the urine, compared to normal controls, might not associate with UTI if compared to urine of ill patients without UTI.

The disclosed nonbiased proteomic identification of a protein profile differentiates UTI from culture negative, no pyuria along with culture negative, pyuria samples.

SUMMARY

Current urinary tract infection (UTI) diagnostic strategies suffer from certain deficiencies. In particular, diagnostic methods that rely on leukocyte esterase have limited accuracy, and culture based methods for identifying UTI suffer the disadvantage of delayed results and also are susceptible to misdiagnoses due to fastidious microorganisms. Therefore, due to the limitation of existing diagnostic procedures, patients are at risk for receiving unneeded antibiotics or delayed treatment resulting in UTI progression.

Using an aptamer based proteomic study, applicant has identified a set of proteins whose detected presence in urine identifies and differentiates a culture positive UTI sample vs culture negative samples. More particularly, applicant has discovered that the proteins C-X-C motif chemokine 6, C-X-C motif chemokine 13, cathepsin S, heat shock 79 kDA protein 1A, mitogen activated protein kinase, protein E7 HPV18 and trangelin represent urine protein biomarkers associated with urinary tract infections.

In accordance with one embodiment urine samples from patients suspected of having a UTI are analyzed for the presence of one or more proteins selected from the group consisting of C-X-C motif chemokine 6, C-X-C motif chemokine 13, cathepsin S, heat shock 79 kDA protein 1A, mitogen activated protein kinase, protein E7 HPV18 and trangelin, wherein the detection of one or more of such proteins in the urine of a patient is indicative of a UTI.

In one embodiment a method of detecting a urinary tract infection in a patient is provided wherein the method comprises the steps of obtaining a urinary sample of a patient to be tested for a urinary tract infection and analyzing the urinary sample to detect the presence of one or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2), wherein the detection of said protein in said urinary sample identifies said patient as having a urinary infection. In one embodiment the urinary sample is screened for the presence of each of the proteins B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2), wherein the detection of this group of proteins in said urinary sample identifies said patient as having a urinary infection. In one embodiment the detection of a 2×, 5× or 10× increase in one or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2) relative to levels detected in a non-UTI urinary sample, wherein the respective proteins levels are normalized to creatinine, is indicative of a UTI.

In accordance with one embodiment the urinary sample is analyzed using any technique known to those skilled in the art for detecting and/or quantifying specific peptides. Such techniques include but are not limited to mass spectroscopy and enzyme-linked immunosorbent assays (ELISA).

In accordance with one embodiment the detection of one or more of the proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2) in the patient's urine sample is used to assist in distinguishing a patient with a urinary tract infection, versus a patient having culture negative pyuria or culture negative no pyuria.

In one embodiment a method for treating a patient having a urinary tract infection is provided wherein the method comprises the steps of identifying a patient having a urinary infection wherein said identification step comprises, obtaining a urine sample from the patient, analyzing said urine sample for the presence of one or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2), wherein the presence of said one or more of these proteins in the urine sample identifies a patient with a urinary tract infection; and treating said identified patients with antibiotics. In accordance with one embodiment the concentration of the proteins is determined and normalized to creatinine levels detected in the sample, wherein detected levels of one or more of B-cell lymphoma 6 protein (BCL6; SEQ ID NO: 23), C-X-C motif chemokine 6 (CXCL6), C-X-C motif chemokine 13 (CXCL13; SEQ ID NO:

29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31), that exceed a threshold value are indicative of a UTI.

In accordance with one embodiment a method of detecting a urinary tract infection in a patient is provided wherein the method comprises obtaining a urinary sample from a patient; and detecting whether a protein profile is present in the urine sample, wherein the protein profile comprises two or more proteins selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31). In one embodiment the protein profile comprises 3, 4, 5, 6, 7 or more of said proteins.

In one embodiment a composition is provided comprising one or more ligands selected from the group consisting of a first ligand that specifically binds to B-cell lymphoma 6 protein (BCL6), a second ligand that specifically binds to C-X-C motif chemokine 6 (CXCL6), a third ligand that specifically binds to C-X-C motif chemokine 13 (CXCL13), a fourth ligand that specifically binds to cathepsin S (CTSS), a fifth ligand that specifically binds to heat shock 70 kDA protein 1A (HSPA1A), a sixth ligand that specifically binds to mitogen activated protein kinase 9 (MAPK9), a seventh ligand that specifically binds to protein E7 HPV18 (E7), and an eighth ligand that specifically binds to transgelin-2 (TAGLN2). In a further embodiment the first, second, third, fourth, fifth, sixth, seventh and eighth ligand are each labeled with a detectable marker.

BRIEF DESCRIPTION OF THE DRAWINGS

FIG. 3 provides a Venn diagram showing the overlap of the identified proteins identified by the three feature selection methods.

FIG. 4A. is a bar graph showing the fold change of proteins identified by Random forest analysis, the dashed line represents a fold change of 1. FIG. 4B provides the UTI class probability estimate for each sample by the optimal SVM classifier. The dashed black line shows where the 50% probability lies. Generally, the data shows that the model probability of predicting UTI samples was >80%. There are 2 outliers, one 18 year old female with CN pyuria (arrow) who presented with left flank pain, fever and dysuria along with 1+LE on UA and had 43.4% UTI probability. The other outlier (arrowhead) was a 3 year old female who presented with fever and abdominal pain, along with 1+LE and had 62.7% UTI probability.

DETAILED DESCRIPTION

DEFINITIONS

Figure 1A:
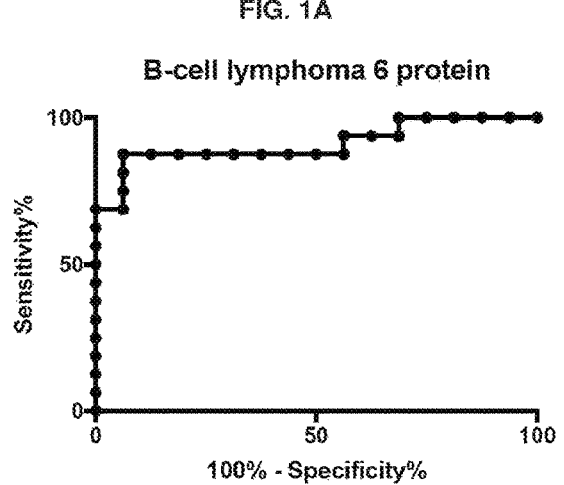
FIGS. 1A-1H: Candidate biomarker ROCs: Area under the curve (AUCs) demonstrating the 8 candidate biomarkers that meet p value filtering criteria and had AUCs>0.9. B-cell lymphoma protein (FIG. 1A), C-X-C motif chemokine 6 (FIG. 1B) C-X-C motif chemokine 13 (FIG. 1C), Cathepsin S (FIG. 1D), Heat shock 79 kDA protein 1A (FIG. 1E), Mitogen activated protein kinase (FIG. 1F), Protein E7 HPV18 (FIG. 1G) and Transgelin 2 (FIG. 1H) are presented.
Figure 1B:
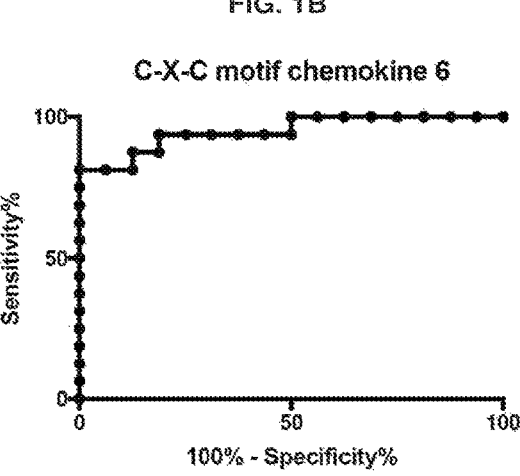
Figure 1B:
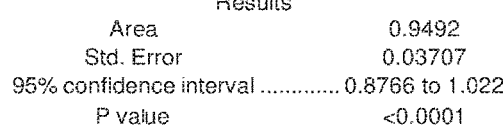
Figure 1C:
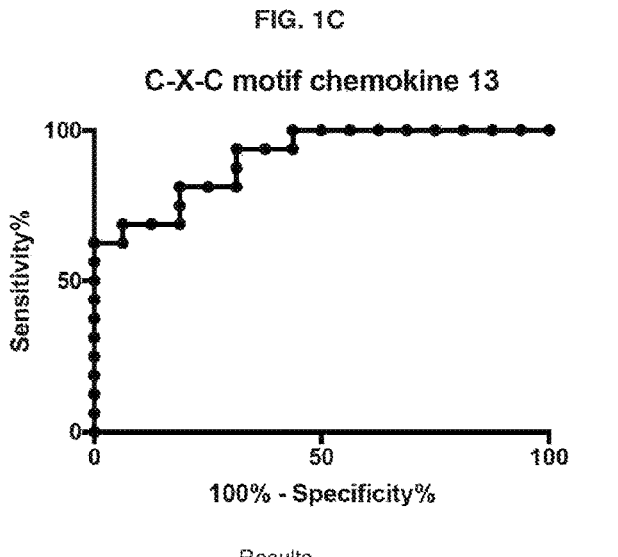
Figure 1D:
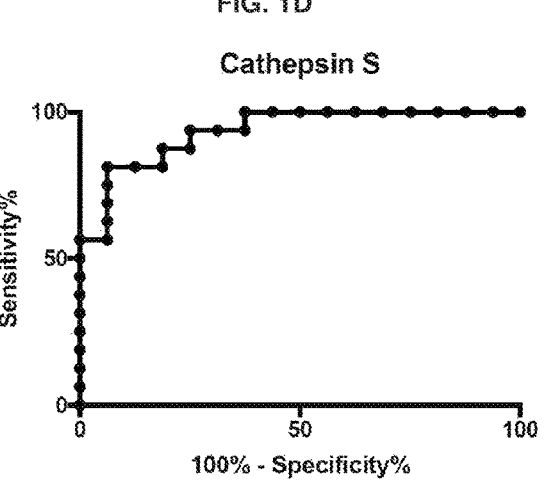
Figure 1D:
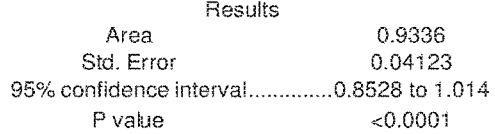
Figure 1E:
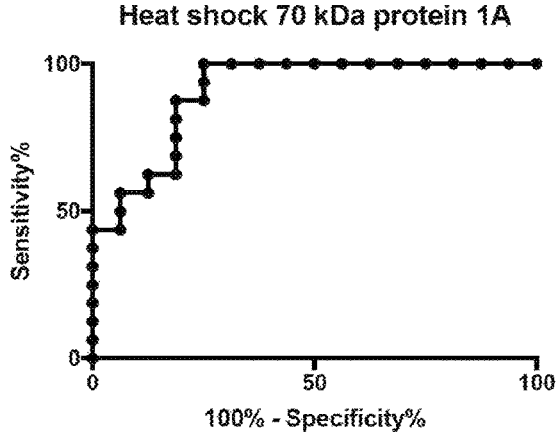
Figure 1F:
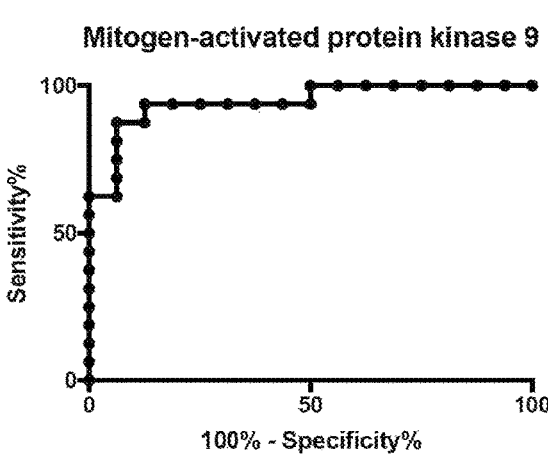
Figure 1G:
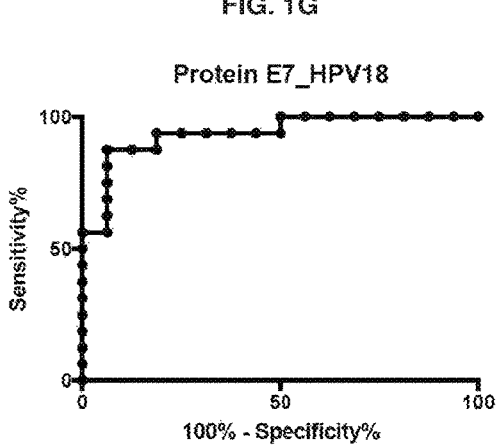
Figure 1G:
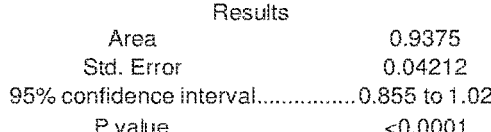
Figure 1H:
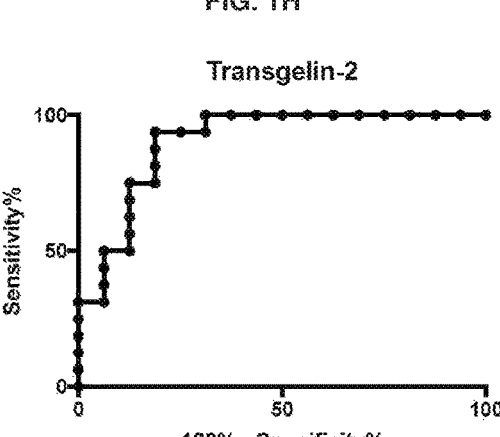
Figure 1H:
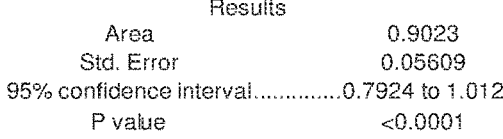
Figure 2A:
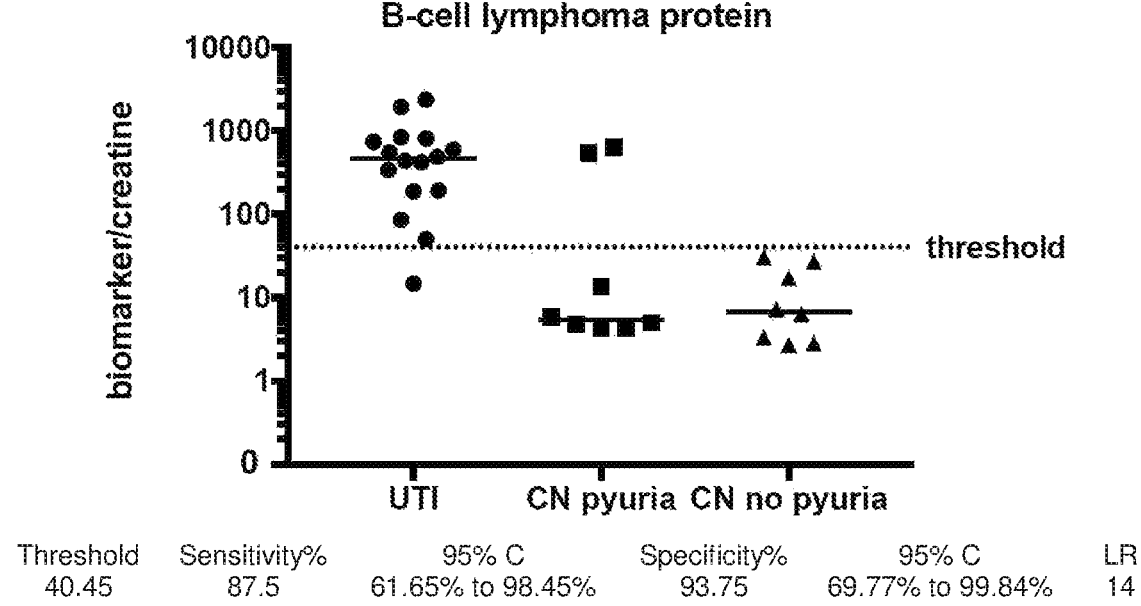
FIGS. 2A-2H: Candidate biomarkers scatterplots: Scatter plots of urine biomarkers that met p value and AUC criteria are presented to show threshold values that differentiate between UTI and no UTI (CN pyuria and CN no pyuria urine). The CN pyuria and CN no pyuria samples were separated for graphical, but not for determination of the likelihood ratio (LR). Threshold levels and LRs are presented for B-cell lymphoma protein (FIG. 2A), C-X-C motif chemokine 6 (FIG. 2B) C-X-C motif chemokine 13 (FIG. 2C), Cathepsin S (FIG. 2D), Heat shock 79 kDA protein 1A (FIG. 2E), Mitogen activated protein kinase (FIG. 2F), Protein E7 HPV18 (FIG. 2G) and Transgelin 2 (FIG. 2H) Biomarker units are relative fluorescent units/ml (RFU) and creatinine units are mg/dl.
Figure 2B:
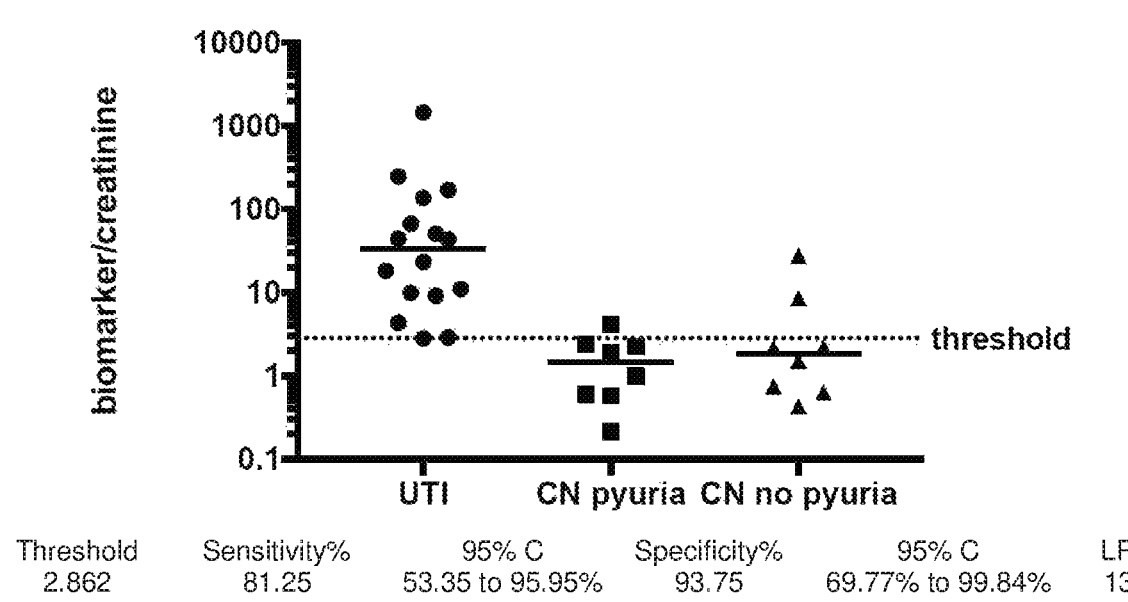
Figure 2C:
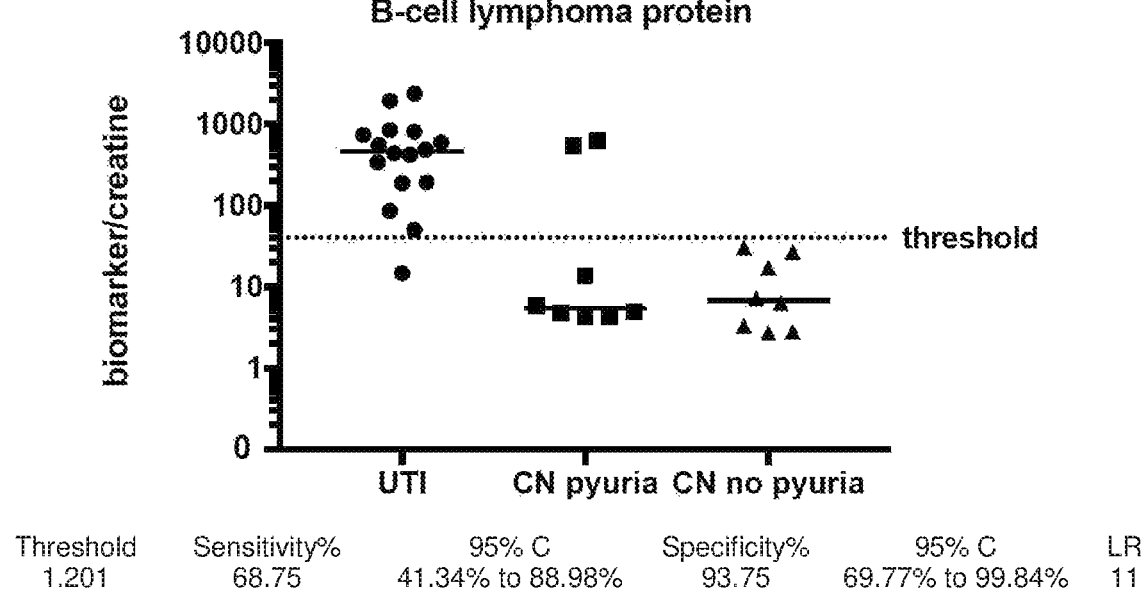
Figure 2D:
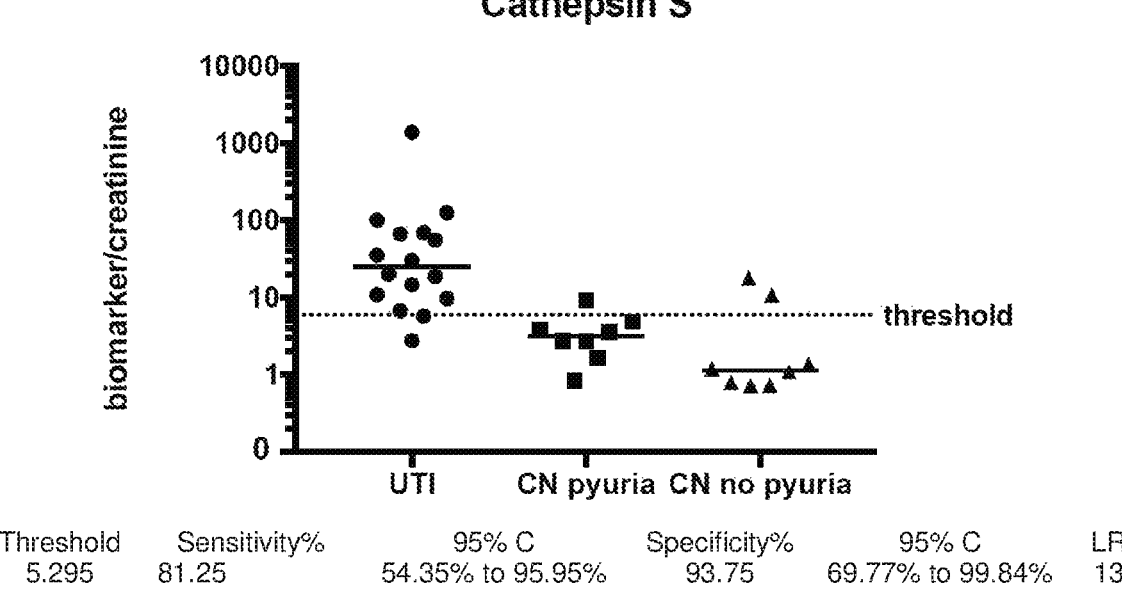
Figure 2E:
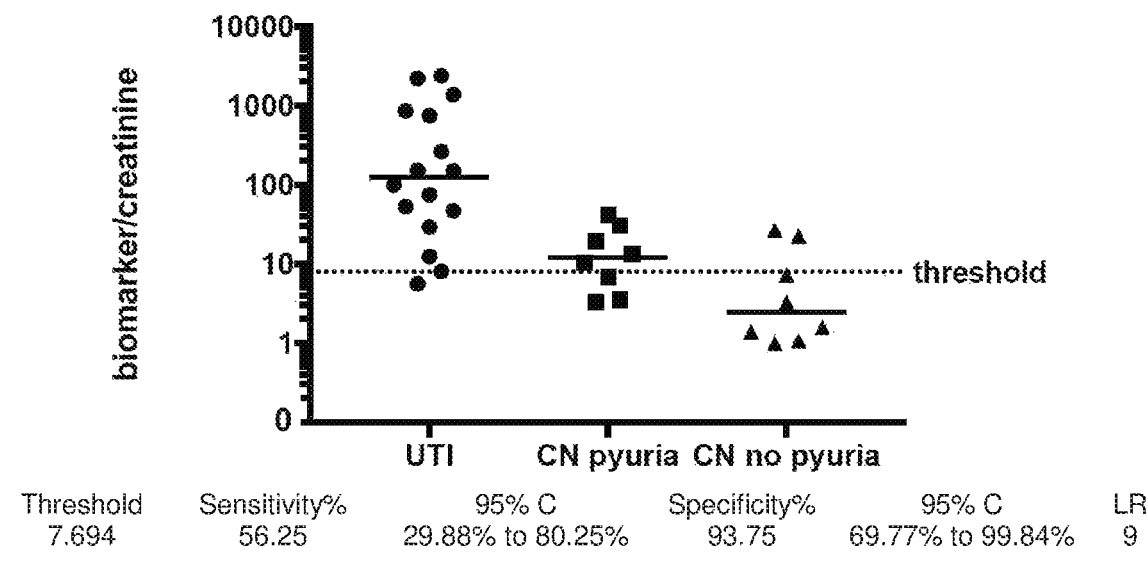
Figure 2F:
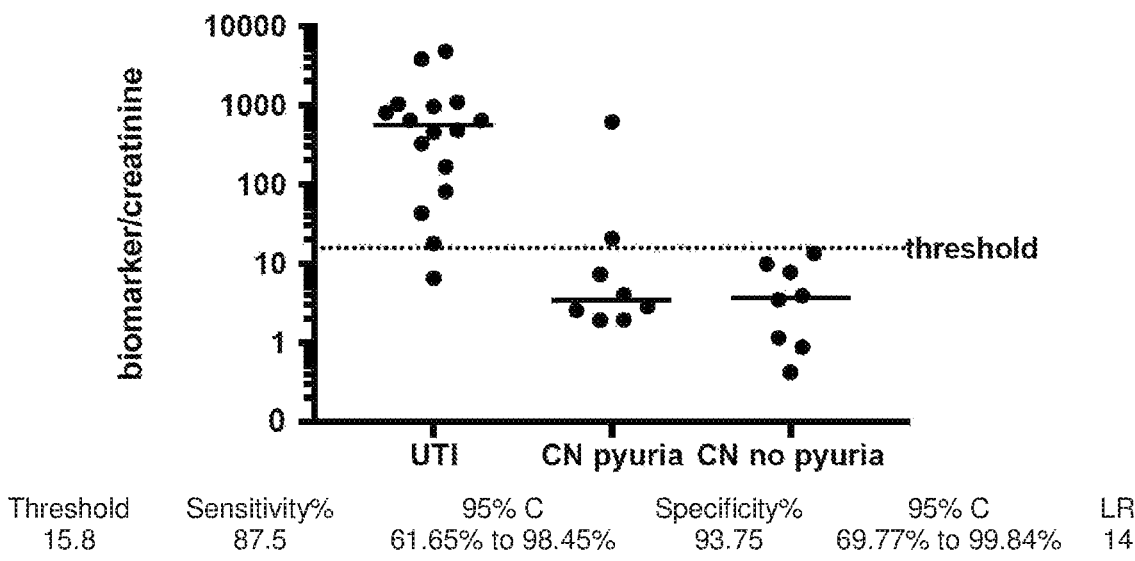
Figure 2G:
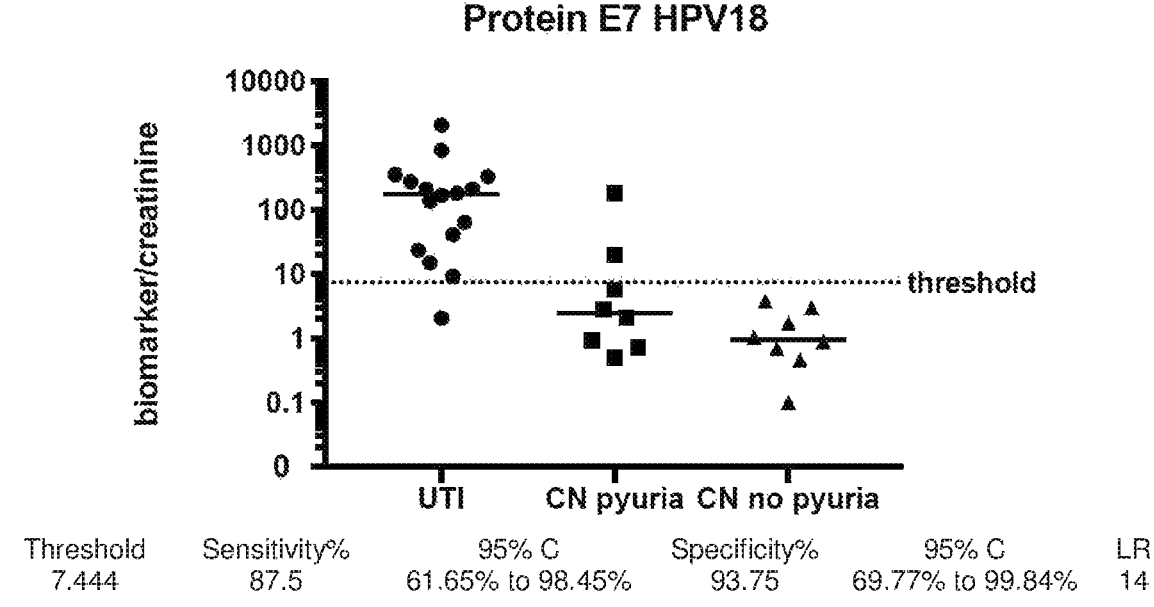
Figure 2H:
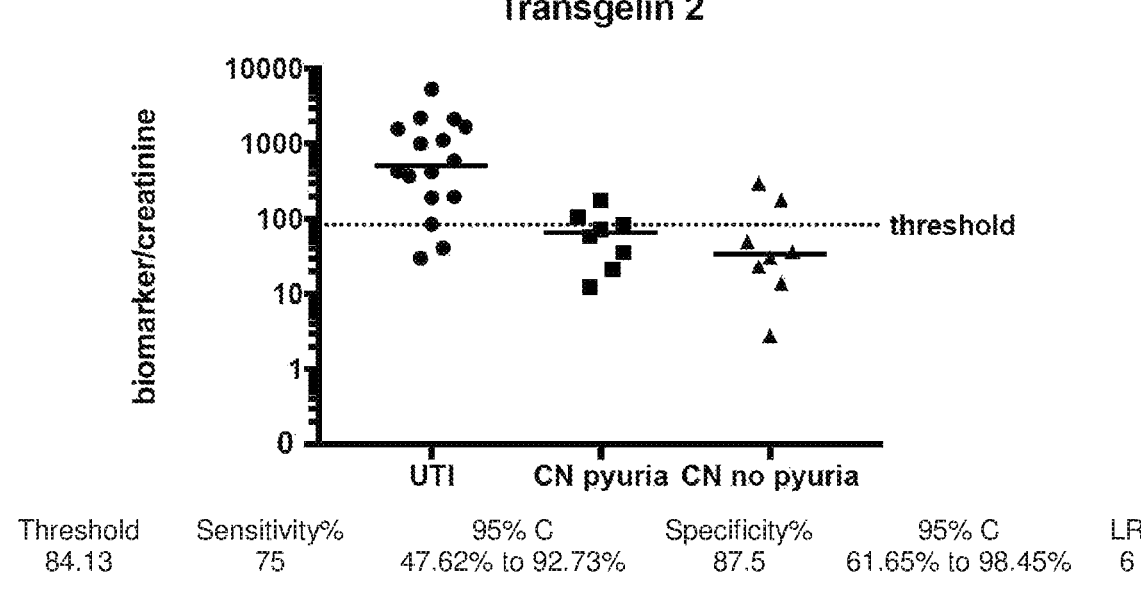

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of an interference RNA of antisense RNA mimetic refers to a nontoxic but sufficient amount of the compound to provide the desired effect. For example one desired effect would be the prevention or treatment of a neurodegenerative disease, as measured, for example, by a decrease in nerve tissue death or decrease in Tau concentrations. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

Sterile Pyuria. There is no universal standard definition for 'Sterile pyuria'. Essentially it is the presence of elevated numbers of white cells in a urine (for our laboratory methods >40 WCC ×106/L), but appears sterile using standard culture techniques.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition. The term "purified RNA" is used herein to describe an RNA sequence which has been separated from other compounds including, but not limited to polypeptides, lipids and carbohydrates.

The term "isolated" requires that the referenced material be removed from its original environment (e.g., the natural environment if it is naturally occurring). For example, a naturally-occurring nucleic acid present in a living animal is not isolated, but the same nucleic acid, separated from some or all of the coexisting materials in the natural system, is isolated.

As used herein the term "patient" without further designation is intended to encompass any warm blooded vertebrate domesticated animal (including for example, but not limited to livestock, horses, mice, cats, dogs and other pets) and humans.

As used herein the term "solid support" relates to a solvent insoluble substrate that is capable of forming linkages (preferably covalent bonds) with soluble molecules. The support can be either biological in nature, such as, without limitation, a cell or bacteriophage particle, or synthetic, such as, without limitation, an acrylamide derivative, glass, plastic, agarose, cellulose, nylon, silica, or magnetized particles. The support can be in particulate form or a monolythic strip or sheet. The surface of such supports may be solid or porous and of any convenient shape.

As used herein, the term "antibody" refers to a polyclonal or monoclonal antibody or a binding fragment thereof such as Fab, F(ab')$_2$ and Fv fragments.

Antibodies as disclosed herein include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules, such asscFv molelcules; and multispecific antibodies formed from antibody fragments.

As used herein, the term "biologically active fragments" of the antibodies described herein encompasses natural or synthetic portions of the respective full-length antibody that retain the capability of specific binding to the target epitope.

As used herein, the term "parenteral" includes administration subcutaneously, intravenously or intramuscularly.

As used herein "an elevated levels of a protein" is considered any detected statistically enhanced concentration of the protein in a patient's urine sample relative to a referenced level of the corresponding protein, wherein the referenced level is based on population data or detected levels in one or more individuals that are free of a urinary tract infection (UTI).

Embodiments

In accordance with one embodiment a method is provided for differentiating patients with a urinary tract infection from patients without a urinary tract infection. In accordance with one embodiment the method comprises the steps of analyzing a urine sample obtained from a patient to determine if the patient has elevated concentrations in the urine sample of one or more proteins having at least 85%, 90% 95% or 99% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31). The proteins may be identified in a point-of-care enzyme linked immunosorbent assay (ELISA), by mass spectroscopy or any other standard protein analysis technique known to those skilled in the art.

In accordance with one embodiment a method is provided to improve the accuracy of diagnosing a urinary tract infection in an adult or pediatric patient by measuring in a urine sample at least one of, or two or more, proteins that have at least 85%, 90%, 95% or 99% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31); normalizing the concentration of each protein to creatinine to account for the concentration of the patient's urine sample to obtain a normalized patient sample; and in the normalized patient sample, diagnosing a urinary tract infection if the protein to creatinine ratio result exceeds a threshold value. The method may be performed at a point of care. A likelihood ratio diagnoses the patient with a urinary tract infection, versus culture negative pyuria, versus culture negative no pyuria.

Accordingly, in one aspect, the present disclosure is directed to methods of diagnosing a urinary tract infection based on the detection of one or more of the proteins that have at least 85%, 90%, 95% or 99% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31) (i.e., the profile proteins) in a patients urine sample. The method of determining a urinary tract infection, versus culture negative pyuria, or versus culture negative no pyuria generally includes obtaining a reference level of the corresponding one or more of the eight listed target proteins, determining the level of the corresponding one or more of the eight listed target proteins (profile proteins) in a sample obtained from the patient and comparing the concentration of the reference protein to the concentration of the corresponding protein in the patient's urine sample. An increase in the expression level of the profile protein in the sample obtained from the patient as compared to the reference expression level indicates the existence of a UTI in the patient. In accordance with one embodiment any increase over a reference threshold concentration is indicative of a UTI. In one embodiment the detection of concentrations of 2, 3, 4, 5, 6, 7 or 8 of the proteins that have at least 85%, 90%, 95% or 99% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31) in a patient's urine sample that are above the corresponding reference threshold is indicative of a UTI. In one embodiment the diagnosis is based on 3, 4, 5, or 6 of the proteins B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2) in a patient's urine sample having concentrations at least 2×, 5× or 10× above the corresponding reference threshold.

In accordance with one embodiment the reference threshold level of the respective protein is obtained based on population data of average concentration levels of the proteins in human patients urine samples. In an alternative embodiment, the reference threshold level of the respective protein is calculated simultaneously with the calculation of the expression level of patient's sample concentration of the protein using a reference sample recovered from individuals devoid of a urinary tract infection. In one embodiment the steps of calculating the reference level comprises the steps of measuring the protein in a reference urine sample, wherein said reference sample is obtained from a patient free of a UTI. Any technique known to those skilled in the art can be used to identify and quantitate the protein levels in the test or reference urine sample. For example, protein concentrations can be quantitatively measured by methods known by those skilled in the art such as Western blotting, enzyme linked immunosorbent assay (ELISA), in situ hybridization, mass spectrometer analysis and combinations thereof. In accordance with one embodiment the detected levels of the proteins are normalized to another component found in human urine, including for example, wherein the respective proteins levels are normalized to creatinine.

In accordance with one embodiment a method of identifying patients with a urinary tract infection is provided wherein the method comprises the steps of obtaining a urinary sample of a patient to be tested for a urinary tract infection;

analyzing that urinary sample to detect the presence of one or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2), wherein the detection of said protein(s) in said urinary sample identifies said patient as having a urinary infection. In accordance with one embodiment the urinary sample is analyzed for the presence of 2 or more, 3 or more, 4 or more, 5 or more, 6 or more, 7 or more or 8 of said proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2). In one embodiment the concentrations of the respective proteins present in a human test urine sample are determined and optionally compared to a reference concentration of the respective proteins found in a urine sample obtained from a non-UTI human. Typically the detected protein concentrations are normalized to another component of the urine, such as creatinine. Patients having detected elevated concentrations of one or more of the eight above listed proteins in their urine relative to a threshold level established by healthy patient's urine sample are diagnosed with having an UTI and are candidates for receiving antibiotic therapeutics. Examples of threshold levels of the respective eight proteins are provided in FIGS. 1A-1H. In one embodiment at least 3, 4, 5, 6, or 7 of the listed eight proteins are required to exceed the threshold levels for an assessment of a UTI to be determined. In one embodiment all eight of the listed eight proteins are required to exceed the threshold levels for an assessment of a UTI to be determined.

In one embodiment a patient's urinary sample is analyzed to determine the concentration of 2, 3, 4 or 5 proteins selected from the group consisting of (BCL6), (CXCL6), (CXCL13), (CTSS), (HSPA1A), (MAPK9), (E7), and (TAGLN2), wherein detected elevated concentrations of the 2, 3, 4 or 5 proteins above the reference threshold levels is diagnostic for a UTI. In one embodiment the detected elevated concentrations of the 2, 3, 4 or 5 proteins are required to be 2×, 5× or 10× above the threshold for a diagnosis of UTI to be assessed.

In accordance with one embodiment the method of diagnosing a urinary tract infection includes analyzing a patient's urine sample for the presence of elevated levels of proteins selected from (BCL6), (CXCL6), (CXCL13), (CTSS), (HSPA1A), (MAPK9), (E7), and (TAGLN2), and further comprising the step of analyzing said urine sample for the presence of an additional protein selected from the group consisting of C-X-C motif chemokine 1 (CXCL1), Non-receptor tyrosine-protein kinase 2 (TYK2), Proteasome activator complex subunit 3 (PSME3), Lactotransferrin (LTF), Histone H2A type 3 (HIST3H2A), Small ubiquitin-related modifier 3 (SUMO3).

In accordance with one embodiment a method for treating a patient having a urinary tract infection is provided. In one embodiment the method comprises the steps of identifying said patient having a urinary infection wherein said identification step comprises obtaining a urine sample from said patient; analyzing said urine sample for the presence of one or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2); wherein the presence of elevated levels said one or more proteins identifies a patient with a urinary tract infection; optionally wherein elevated levels of 2, 3, 4, 5, 6, 7 or 8 of those proteins is determined to exceeds the threshold levels of a corresponding reference protein level; and then treating said identified patients with antibiotics.

In one embodiment the detected concentration of 1, 2, 3, 4, 5, 6, 7 or 8 of the proteins (BCL6), (CXCL6), (CXCL13), (CTSS), (HSPA1A), (MAPK9), (E7), and (TAGLN2) must be at least 2X relative to the threshold level to lead to a diagnosis of a UTI. In one embodiment the detected concentration of 1, 2, 3, 4, 5, 6, 7 or 8 of the proteins (BCL6), (CXCL6), (CXCL13), (CTSS), (HSPA1A), (MAPK9), (E7), and (TAGLN2) must be at least 5X relative to the threshold level to lead to a diagnosis of a UTI. In one embodiment the concentration of three or more of the proteins (BCL6), (CXCL6), (CXCL13), (CTSS), (HSPA1A), (MAPK9), (E7), and (TAGLN2) are determined and all three must exceed their respective threshold levels to lead to a diagnosis of a UTI. In one embodiment the concentration of four or more of the proteins (BCL6), (CXCL6), (CXCL13), (CTSS), (HSPA1A), (MAPK9), (E7), and (TAGLN2) are determined and all four must exceed their respective threshold levels to lead to a diagnosis of a UTI. In one embodiment the concentration of five or more of the proteins (BCL6), (CXCL6), (CXCL13), (CTSS), (HSPA1A), (MAPK9), (E7), and (TAGLN2) are determined and all five must exceed their respective threshold levels to lead to a diagnosis of a UTI. In one embodiment the concentration of six or more of the proteins (BCL6), (CXCL6), (CXCL13), (CTSS), (HSPA1A), (MAPK9), (E7), and (TAGLN2) are determined and all six must exceed their respective threshold levels to lead to a diagnosis of a UTI. In one embodiment the concentration of seven or more of the proteins (BCL6), (CXCL6), (CXCL13), (CTSS), (HSPA1A), (MAPK9), (E7), and (TAGLN2) are determined and all seven must exceed their respective threshold levels to lead to a diagnosis of a UTI. In one embodiment the concentration of all eight of the proteins (BCL6), (CXCL6), (CXCL13), (CTSS), (HSPA1A), (MAPK9), (E7), and (TAGLN2) are determined and all eight must exceed their respective threshold levels to lead to a diagnosis of a UTI. In one embodiment the detected concentration of 1, 2, 3, 4, 5, 6, 7 or 8 of (BCL6), (CXCL6), (CXCL13), (CTSS), (HSPA1A), (MAPK9), (E7), and (TAGLN2) must be at least 2X relative to the threshold level.

In one embodiment the detected concentration of 1, 2, 3, 4, 5, 6, 7 or 8 of (BCL6), (CXCL6), (CXCL13), (CTSS), (HSPA1A), (MAPK9), (E7), and (TAGLN2) must be at least 2X relative to the corresponding threshold level of that protein, and at least 2, 3, 4 or 5 of (BCL6), (CXCL6), (CXCL13), (CTSS), (HSPA1A), (MAPK9), (E7), and (TAGLN2) must be at least 5X relative to the threshold level for the respective proteins to lead to a diagnosis of a UTI. In one embodiment the concentration of all eight of the proteins (BCL6), (CXCL6), (CXCL13), (CTSS), (HSPA1A), (MAPK9), (E7), and (TAGLN2) are determined and all eight must exceed their respective threshold levels by at least 2X and optionally the detected concentration of 3, 4 or 5 of (BCL6), (CXCL6), (CXCL13), (CTSS), (HSPA1A), (MAPK9), (E7), and (TAGLN2) must be at least 5X relative to the threshold level to lead to a diagnosis of a UTI.

In one embodiment the method of identifying a patient as having a UTI comprises the steps of obtaining a reference level of one or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2); and determining the concentration of the corresponding one or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2) in said urine sample; wherein a detected higher level of one or more of said proteins in said urine sample relative to the corresponding reference levels indicates the patient has a urinary tract infection. In one embodiment the reference level is established based on urinary samples recovered from humans that do not have a UTI. In one embodiment the detected concentration of the (BCL6), (CXCL6), (CXCL13), (CTSS), (HSPA1A), (MAPK9), (E7), and (TAGLN2) proteins is normalized to creatinine.

In one embodiment a method of detecting a urinary tract infection in a patient is provided wherein the method comprises obtaining a urinary sample from a patient; and detecting whether a protein profile is present in the urine sample wherein the protein profile comprises two or more proteins selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2). In accordance with one embodiment the protein profile comprises 2 or more of said proteins, wherein the detected protein concentration of each of the 2 or more proteins in the patient urine sample exceeds the corresponding reference threshold value. In accordance with one embodiment the protein profile comprises 3 or more of said proteins, wherein the detected protein concentration of each of the 3 or more proteins in the patient urine sample exceeds the corresponding reference threshold value. In accordance with one embodiment the protein profile comprises 4 or more of said proteins, wherein the detected protein concentration of each of the 4 or more proteins in the patient urine sample exceeds the corresponding reference threshold value. In accordance with one embodiment the protein profile comprises 5 or more of said proteins, wherein the detected protein concentration of each of the 5 or more proteins in the patient urine sample exceeds the corresponding reference threshold value. In accordance with one embodiment the protein profile comprises 6 or more of said proteins, wherein the detected protein concentration of each of the 6 or more proteins in the patient urine sample exceeds the corresponding reference threshold value. In accordance with one embodiment the protein profile comprises 7 or more of said proteins, wherein the detected protein concentration of each of the 7 or more proteins in the patient urine sample exceeds the corresponding reference threshold value. In accordance with one embodiment the protein profile comprises all 8 of said proteins, wherein the detected protein concentration of each of the 8 proteins in the patient urine sample exceeds the corresponding reference threshold value.

In accordance with one embodiment a composition is provided for detecting one or more of the proteins (BCL6), (CXCL6), (CXCL13), (CTSS), (HSPA1A), (MAPK9), (E7), and (TAGLN2). In one embodiment the composition comprises a ligand that specifically binds to protein selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2). In one embodiment the composition comprises two or more different ligands, wherein each of the different ligands specifically binds to a different protein selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2). In one embodiment the ligand is an antibody, including for example a monoclonal antibody or fragment thereof. In one embodiment the ligand is labeled with a detectable marker including for example a fluorophore, radioactive isotope or alternatively or additionally labeled with an affinity tag such as a biotin, avidin, streptavidin or His tag. The ligands may also be linked to a solid support.

In accordance with one embodiment a composition is provided wherein the composition comprises a first and second ligand, wherein the first and second ligand each specifically binds to a different protein selected from the group consisting of B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), and transgelin-2 (TAGLN2). In one embodiment the composition the first and second ligand are labeled with a detectable marker, and in one embodiment the ligands are antibodies, optionally monoclonal antibodies. In one embodiment the antibodies are labeled with a detectable marker and/or are covalently linked to a solid support.

In one embodiment a composition is provided, wherein the composition comprises 1, 2, 3, 4, 5, 6, 7, or 8 of the following: a first ligand that specifically binds to B-cell lymphoma 6 protein (BCL6), a second ligand that specifically binds to C-X-C motif chemokine 6 (CXCL6), a third ligand that specifically binds to C-X-C motif chemokine 13 (CXCL13), a fourth ligand that specifically binds to cathepsin S (CTSS), a fifth ligand that specifically binds to heat shock 70 kDA protein 1A (HSPA1A), a sixth ligand that specifically binds to mitogen activated protein kinase 9 (MAPK9), a seventh ligand that specifically binds to protein E7 HPV18 (E7), and an eighth ligand that specifically binds to transgelin-2 (TAGLN2), optionally wherein each of said first, second, third, fourth, fifth, sixth, seventh and eighth ligand are labeled with a detectable marker and/or covalently linked to a solid support.

One embodiment of the present disclosure is directed to a urine protein signature comprising the proteins selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31) or corresponding proteins that have at least 85% , 90%, 95% or 99% sequence identity to those proteins differentiating urinary tract infections from culture negative urine samples regardless of pyuria status.

One embodiment is a diagnostic to identify and quantitate B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), transgelin-2 (TAGLN2) in a urine sample to assess the likelihood of a urinary tract infection in a patient, where the diagnostic uses a rapid polymerase chain reaction (PCR) assay.

One embodiment is a diagnostic to identify and quantitate B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), transgelin-2 (TAGLN2) in a urine sample to assess the likelihood of a urinary tract infection in a patient, where the diagnostic uses paper spray mass spectroscopy.

One embodiment is a diagnostic to identify and quantitate B-cell lymphoma 6 protein (BCL6), C-X-C motif chemokine 6 (CXCL6), C-X-C motif chemokine 13 (CXCL13), cathepsin S (CTSS), heat shock 70 kDA protein 1A (HSPA1A), mitogen activated protein kinase 9 (MAPK9), protein E7 HPV18 (E7), transgelin-2 (TAGLN2) in a urine sample to assess the likelihood of a urinary tract infection in a patient, where the diagnostic uses a lateral flow assay.

In any of these embodiments, the patient may be a pediatric patient.

The UTI probability is predicted as percent likelihood, with clinician use to make the decision whether or not to initiate therapy. In one embodiment the predictive model is applied at the point of care by analyzing the patient's urine sample using paper spray mass spectroscopy, lateral flow assay, or a rapid PCR ProQuantum® (ThermoFisher Scientific Waltham Mass. ) immunoassay as a feasible clinical test. Conversion of a urine biomarker panel to a point of care testing protocol increases UTI diagnostic accuracy, and thus limiting the use of unneeded antibiotics.

Aptamer based proteomics analysis (See Example 1) reveals a urine protein signature that differentiates culture proven urinary tract infections from culture negative samples, regardless of pyuria status. Urine biomarker protein to creatinine levels were filtered differences (p value<0.01) between the UTI versus culture negative (no pyuria) and UTI versus culture negative (pyuria) and an area under the curve of >0.9. Threshold urine biomarker to creatinine levels that had the highest likelihood ratio of diagnosing UTIs were determined. Machine learning was performed to determine the combination of biomarkers that optimized diagnostic accuracy. mRNA and protein expression patterns of a subset of candidate biomarkers were also determined.

The following eight candidate urine protein biomarkers met filtering criteria:
B-cell lymphoma 6 protein (BCL6)
C-X-C motif chemokine 6 (CXCL6)
C-X-C motif chemokine 13 (CXCL13)
cathepsin S (CTSS)
heat shock 70 kDA protein 1A (HSPA1A)
mitogen activated protein kinase 9 (MAPK9)
protein E7 HPV18 (E7)
transgelin-2 (TAGLN2)

AUCs ranged from 0.9063 to 0.9492 and likelihood ratios to distinguish UTI from not UTI ranged from 6-14. Supervised vector machine learning algorithms were applied and determined a model to predict UTI.

EXAMPLE 1

Identification of a Urine Protein Signature

Biomarkers are clinically relevant from target validation in the laboratory, to patient classification in the clinic. Difficulty developing high throughput assays (e.g. enzyme-linked immunosorbent assay (ELISA) or protein coated bead assays) for assessing biomarker candidates against large clinical sample collections have hindered application. SOMAscan® (Somologics, Boulder Colo.) uses slow-off-rate modified aptamer (SOMAmer®) protein binding reagents. Aptamers are modified DNA with high affinity (109-1012 M) and high specificity for their cognate analytes comparable to sandwich ELISA performance. Use of the SOMAscan® platform established unique protein profiles in autoimmune cholangitis. The SOMAscan® platform here compared (a) children with no growth on culture or LE, (b) children with pyuria and no growth on urine culture and (c) children with pyuria and 50,000 cfu/ml of *E. coli* on urine culture, and revealed a protein profile unique to children with UTI.

A urine sample was obtained from sixteen (16) pediatric emergency room patients and both pyuria and cultures were performed on each sample; the sample for urine culture was an aliquot obtained by clean catch. Eight (8) of these patients had culture negative pyuria, i.e., positive leukocyte esterase on urinalysis results but negative urine culture results, and eight (8) of these patients had normal urinalysis results and normal culture results, that is, negative for both pyuria and culture.

Aptamer based proteomics were performed in these sixteen samples, levels of 1,310 proteins were quantified as relative fluorescent units (RFU)/ml using the SOMAscan® platform (Somalogic Inc. Boulder Colo.), and protein levels were normalized to urine creatinine (mg/dl). Aptamers are modified DNA with high affinity ($10^9$M-$10^{12}$ M) and high specificity for their cognate analytes, comparable to sandwich ELISA performance that have been used for biomarker discovery, described in reference.

Results were filtered using stringent criteria (p<0.01) to identify proteins that were significantly higher in the UTI versus culture negative pyuria samples and in the UTI versus normal urine samples with a p value of <0.01, and that had an area under the curve (AUC) of >0.9, specifically between 0.9063 and 0.9492, which according to the literature defines an "excellent" biomarker. Addition of urine innate immune protein levels adds a distinct biomarker mechanism to current UTI diagnosis methods. Eight proteins were identified from this stringent screening. Identification and quantitation of at least these eight proteins, normalized to urine creatinine to account for different concentrations of urine in different individuals, yielded the highest likelihood to timely and accurately differentiate samples from patients with a urinary tract infection, from samples from patients without a urinary tract infection; that is, to differentiate UTI versus non-UTI samples.

EXAMPLE 2

Aptamer Based Proteomic Study

An aptamer based proteomic study was conducted to identify urine protein levels that could differentiate a culture proven UTI from culture negative samples regardless of pyuria status.
Methods
Samples were prospectively obtained in the Emergency Department and main campus Urgent Care at Nationwide Children's Hospital, Columbus, Ohio. Inclusion criteria consisted of dipstick urinalysis and urine culture performed for any clinical indication and availability of excess urine sample. Exclusion criteria consisted antibiotic treatment within 7 days before ED presentation. Human kidney, bladder and spleen tissue was obtained from the Cooperative Tissue Network, Midwest Division (Columbus, Ohio) using Nationwide Children's Hospital IRB IRB07-00383.
Sample Collection and Processing:
After ensuring sufficient urine volume was available for clinical diagnostic tests, excess urine was immediately collected in AssayAssure urine collection tubes (Thermo Scientific, Waltham, Mass.) containing a bacteriostatic preservative that suppresses nuclease and protease activity and preserves urine specimens at room temperature for up to 26 days according to the manufacturer; we independently confirmed protein stability for 14 days. Samples were processed within 7 days of collection by centrifuged at 3,000 rpm for 5 min with the supernatant saved in 300 ul to 500 ul aliquots and stored at −80° C.

Groups:

Eight clean catch urine samples were selected for each of the following patient groups:

(a) UTI defined by greater than 1+LE on urine dipstick and greater than 50,000 cfu/ml of *E. coli* on urine culture;

(b) Culture negative (CN) pyuria defined by greater than 1+LE on urine dipstick and no growth on urine culture; and (c) CN no pyuria defined by negative LE on urine dipstick and no growth on urine culture.

The UTI group was divided between those with and without fevers >100.4° F/38° C. (either in the ED or at home by report).

Urine proteomic evaluation: One aliquot of the selected samples were sent on dry ice to Somalogic Inc (Boulder, CO) where SOMAscan analysis was performed to measure concentrations of 1,310 proteins in the assay at the time. The SOMAscan results are presented as relative fluorescent units (RFU) per ml. Urine protein levels were normalized to urine creatinine which were measured using the Oxford colorimetric assay (Oxford Biomedical Research, Oxford, Mich.) in the Schwaderer lab and presented as mg per dl. Final results were presented as biomarker (RFU/ml) to creatinine (mg/dl) ratios.

mRNA and protein expression patterns:

RNA purification from tissues was performed using a RNeasy plus kit (Qiagen, CA), quantity and purity was measured using a Nanophotometer NP80 (Implen, CA) and cDNA was generated. cDNA was amplified using the Quantstudio 3 (Applied Biosystems, CA). Relative mRNA expression was quantified using the $2^{-\Delta\Delta C_T}$ methodology. Primers used are listed below in Table 1:

TABLE 1

| Gene | Primer | Sequence | SEQ ID NO |
|---|---|---|---|
| GUSB | forward | ACTGAACAGTCACCGAC | 1 |
| | reverse | AAACATTGTGACTTGGCTAC | 2 |
| BCL6 | forward | ATTGTGAGAAGTGTAACCTG | 3 |
| | reverse | TTTGGGTAGATTCTGAGAAGG | 4 |
| CXCL1 | forward | ATGCTAGAACAGTGACAAATC | 5 |
| | reverse | TCTTCTGTTCCTATAAGGGC | 6 |
| HSPA1A | forward | AATTTCCTGTGTTTGCAATG | 7 |
| | reverse | AAAATGGCCTGAGTTAAGTG | 8 |
| MAPK9 | forward | TCAGATGCAGCAGTAAGTAG | 9 |
| | reverse | AGGTGAGAGTTCCTTCAATG | 10 |
| CTSS | forward | TCTACAGAAGTGGTGTCTAC | 11 |
| | reverse | CCTTTATTTCTTGCCATCCG | 12 |
| MMP1 | forward | AAAGGGAATAAGTACTGGGC | 13 |
| | reverse | CAGTGTTTTCCTCAGAAAGAG | 14 |
| CXCL13 | forward | CATAGTCTGGAAGAAGAACAAG | 15 |
| | reverse | AAGAATGCAGGTGTTCTTAG | 16 |
| TAGLN2 | forward | CACTGACATCTTCCAAACTG | 17 |
| | reverse | CCTTGGATTTCTTAGGGAAC | 18 |

TABLE 1-continued

| Gene | Primer | Sequence | SEQ ID NO |
|---|---|---|---|
| HPV18-E7 | forward | TGCATGGACCTAAGGCAA | 19 |
| | reverse | GCTGGGATGCACACCA | 20 |
| HIST2H2A | forward | TTTCCTTGACTCGGAAATG | 21 |
| | reverse | TCCGAATAGTTGCCCTTG | 22 |

Immunohistochemistry images for were obtained from the Human Protein Atlas version 18.1.

Statistical Analysis:

Epidemiology and presenting symptoms were compared with the chi square test if percentages or proportions were evaluated using Graphpad Prism (La Jolla, Calif.). For continuous data parametric distribution was confirmed using the D'Agostino & Pearson test. Groups were compared by the Wilcoxon test with SPSS software (IBM corporation, Armonk N.Y.) . Proteins were filtered by the following criteria:

a) significantly different between the UTI group (febrile and afebrile combined) vs the CN pyuria group;

b) and also different between the UTI group (febrile and afebrile combined) vs the CN no pyuria group;

c) but not different between the CN pyuria group vs CN no pyuria group. Significance was assigned for a p value of <0.01. Next proteins with that met the p value filtering criteria were filtered for a 1 way ANOVA Area under curve (AUC) of >0.9. A general guide for interpreting the utility of a biomarker based on AUC is: fail=0.5-0.6, poor=0.6-0.7, fair=0.7-0.8, good=0.8-0.9 and excellent=0.9-1.0.

Support Vector Machine (SVM) Predictive Model Optimization:

Feature selection plays a crucial role in biomedical data mining. Three different feature selection approaches were considered to reduce the data dimensionality before the model was trained on training subset in each fold of inner leave-one-out cross-validation:

(a) feature selection based on the Wilcoxon rank sum test to screen proteins with expression strongly associated with UTI.

(b) Feature ranking on the basis of random forest feature importance scores computed from the Gini impurity reduction.

(c) ReliefF feature selection techniques. Considering the limitation of the sample size, hyperparameter tuning and model optimization was performed using leave-one-out cross-validation in an inner loop. We conducted a grid search to explore the optimal hyperparameter space including a range of values for gamma and/or C for support vector classifiers with either linear or RBF kernel. The accuracy was calculated at each cross-validation split on the validation set. The mean accuracy was used as a metric for model selection. To assess the predictive performance, we further computed the performance estimates of our models on unseen data (test set) using 5-fold cross-validation in the outer loop. The overall unbiased generalization performance of the optimal model was evaluated by the mean area under the curve (AUC) values of the receiver operating characteristic (ROC) curve, obtained in each iteration of the cross-validation split. The class probability estimate of each sample was calculated based on decision values of SVM using the parameters learned in Platt scaling. A number of Python libraries and R packages were used in data analysis and machine learning processes including Pandas, Scikit-Learn, skrebate, ggplot2, dplyr, ROCR, and pROC.

Figure generation: Figures were generated using Graph-pad Prism, Microsoft Powerpoint (Microsoft corporation, Redomond, Wash.) or by web-based Lucidchart tool (https://www.lucidchart.com).

Results

We included urine samples from 32 patients (4 males and 28 females) with a median age of 7.1 years (25% and 75% of 4.7 and 14.0 respectively). Sixteen patients were assigned to a UTI group, 8 patients to the culture negative pyuria group and 8 patients to the CN no pyuria.

The UTI group was evenly divided between those with and without fevers>100.4° F/38° C. (either in the ED or at home by report). No patients were immunosuppressed, 2 patients in the UTI group had a history of kidney stones and 1 patients in the UTI group, a now 5 year old, had a history of congenital hydronephrosis. There were no statistical significance differences in age, sex or presenting symptoms between groups with the exception of a higher percentage of patients with fever in the UTI compared to the CN no pyuria group (Table 2).

TABLE 2 epidemiology and presenting symptoms[1] of groups

| | UTI (n = 16) | CN pyuria (n = 8) | CN no pyuria (n = 8) | P value |
|---|---|---|---|---|
| Age (years) | 8.2 ± 4.7 | 11.4 ± 5.9 | 7.2 ± 4.2 | 0.217 |
| Female:male | 15:1 | 7:1 | 5:3 | 0.133 |

TABLE 2-continued epidemiology and presenting symptoms[1] of groups

| | UTI (n = 16) | CN pyuria (n = 8) | CN no pyuria (n = 8) | P value |
|---|---|---|---|---|
| (% female) | (94%) | (88%) | (63%) | |
| Fever | 8 (50%) | 2 (25%) | 0 (0%) | *0.041 |
| Dysuria | 5 (31%) | 2 (25%) | 3 (38%) | 0.793 |
| Frequency | 4 (25%) | 1 (13%) | 0 (0%) | 0.272 |
| Urgency/enuresis | 4 (25%) | 2 (25) | 1 (13%) | 0.760 |
| Suprapubic pain | 4 (25%) | 1 (13%) | 0 (0%) | 0.272 |
| Abdominal pain | 8 (50%) | 4 (50%) | 3 (38%) | 0.828 |
| Back/flank pain | 2 (13%) | 3 (38%) | 0 (0%) | 0.105 |

[1]other presenting symptoms included syncope (1 in UTI group and one in normal U urine group, bump on testicle (1 in CN no pyuria group), headache (one in normal urine group), foul smelling urine (1 in normal urine group) and memory loss (1 in CN pyuria group)
*statistically significant, p < 0.05 with the significant difference between UTI and CN no pyuria group.

Identification of Proteins Elevated During UTI

We identified 133 proteins that were significantly elevated (p value<0.05) in UTI vs the culture negative pyuria comparison and the UTI vs the CN no pyuria group but were not statistically different when the CN pyuria group was compared to the CN no pyuria urine group. To focus on the most differential proteins between groups, we filtered for a p value<0.01 and identified 32 proteins that were elevated in the UTI group, but not the CN-pyuria or CN no pyuria groups (Table 3).

10

TABLE 3

Urine biomarker levels (urine biomarker (relative fluorescent units)/urine creatinine (mg))

| | | | | p value | | |
|---|---|---|---|---|---|---|
| Protein | Median CN no pyuria | Median CN pyuria | Median UTI | UTI vs CN-no pyuria | UTI vs CN-pyuria | CN-no pyuria vs CN-pyuria |
| Alpha-2-macroglobulin | 812 ± 1055 | 1170 ± 2104 | 15462 ± 153990 | 0.001 | 0.006 | 0.442 |
| B-cell lymphoma 6 protein | 678 ± 1132 | 542 ± 27213 | 46537 ± 656650 | <0.001 | 0.006 | 0.721 |
| BH3-interacting domain death agonist | 341 ± 1900 | 630 ± 263 | 33323 ± 6533 | 0.006 | <0.001 | 0.234 |
| C-X-C motif chemokine 11 | 55.12 ± 439 | 3604 ± 548 | 1331 ± 95541 | 0.005 | 0.001 | 0.328 |
| C-X-C motif chemokine 13 | 44 ± 972 | 80 ± 163 | 474 ± 8735 | <0.001 | 0.003 | 0.195 |
| C-X-C motif chemokine 6 | 185 ± 942 | 145 ± 131 | 3342 ± 35842 | 0.001 | <0.001 | 0.645 |
| Calcium/calmodulin-dependent protein kinase type 1 | 1452 ± 3393 | 2126 ± 1951 | 8080 ± 18809 | 0.004 | 0.009 | 0.328 |
| Cathepsin S | 114 ± 645 | 314 ± 255 | 2513 ± 33882 | <0.001 | <0.001 | 0.195 |
| Endothelial monocyte-activating polypeptide 2 | 277 ± 698 | 394 ± 295 | 1788 ± 5360 | 0.002 | 0.006 | 0.382 |
| Granulocyte-macrophage colony-stimulating factor | 44 ± 111 | 46 ± 40 | 296 ± 930 | 0.004 | <0.001 | 0.959 |
| Gro-beta/gamma | 162 ± 843 | 377 ± 259 | 6564 ± 93973 | 0.002 | 0.001 | 0.161 |
| Growth-regulated alpha protein | 287 ± 1952 | 1490 ± 1675 | 27124 ± 146868 | <0.001 | 0.002 | 0.195 |
| Heat shock 70 kDa protein 1A | 244 ± 1044 | 1190 ± 1379 | 12440 ± 78706 | <0.001 | 0.003 | 0.083 |
| Heat shock cognate 71 kDa protein | 5838 ± 30168 | 18610 ± 13963 | 69018 ± 160844 | 0.002 | 0.003 | 0.382 |
| Histone H2A type 3 | 5148 ± 7319 | 6517 ± 42825 | 56331 ± 130985 | 0.001 | 0.005 | 0.574 |
| Immunoglobulin A | 39421 ± 73514 | 30451 ± 67150 | 222417 ± 221679 | 0.009 | 0.007 | 0.878 |
| Interstitial collagenase | 55.8 ± 1.30 | 94 ± 5270 | 890 ± 33547 | <0.001 | 0.009 | 0.130 |
| Macrophage-capping protein | 1917 ± 6597 | 1899 ± 1555 | 33978 ± 107421 | 0.004 | 0.001 | 0.878 |
| Mitogen-activated protein kinase 9 | 371 ± 478 | 346 ± 21489 | 55799 ± 136700 | <0.001 | 0.001 | 0.574 |
| Mothers against decapentaplegic homolog 3 | 164 ± 535 | 204 ± 189 | 1162 ± 1576 | 0.009 | 0.004 | 0.645 |
| Nucleoside diphosphate kinase A | 1850 ± 10050 | 3016 ± 4232 | 45384 ± 429.0 | 0.003 | 0.007 | 0.645 |
| Proteasome activator complex subunit 1 | 1800 ± 7904 | 1590 ± 1585 | 27296 ± 74459 | 0.005 | 0.001 | 0.798 |
| Proteasome activator complex subunit 3 | 54 ± 57 | 73 ± 244 | 773 ± 2986 | 0.001 | 0.007 | 0.382 |

TABLE 3-continued

Urine biomarker levels (urine biomarker (relative fluorescent units)/urine creatinine (mg))

| | | | | p value | | |
|---|---|---|---|---|---|---|
| Protein | Median CN no pyuria | Median CN pyuria | Median UTI | UTI vs CN-no pyuria | UTI vs CN-pyuria | CN-no pyuria vs CN-pyuria |
| Protein E7_HPV18 | 96 ± 131 | 247 ± 6253 | 17510 ± 51559 | <0.001 | 0.001 | 0.195 |
| Pulmonary surfactant-associated protein D | 9529 ± 45588 | 15407 ± 33968 | 185604 ± 371714 | 0.005 | 0.007 | 1.000 |
| Ras GTPase-activating protein 1 | 55 ± 225 | 74 ± 49 | 486 ± 1565 | 0.004 | <0.001 | 0.721 |
| Small nuclear ribonucleoprotein F | 141 ± 295 | 336 ± 183 | 1155 ± 9453 | 0.002 | 0.007 | 0.279 |
| Stress-induced-phosphoprotein 1 | 1331 ± 15285 | 1889 ± 3156 | 31714 ± 142272 | 0.005 | 0.001 | 0.721 |
| Tissue-type plasminogen activator | 1828 ± 1290 | 360 ± 724 | 2326 ± 15039 | 0.004 | 0.004 | 0.645 |
| Transgelin-2 | 3383 ± 10436 | 6614 ± 5343 | 50796 ± 135169 | 0.001 | 0.001 | 0.645 |
| Tumor necrosis factor receptor superfamily member 13C | 180 ± 593 | 324 ± 242 | 1649 ± 3945 | 0.002 | 0.001 | 0.382 |
| Ubiquitin carboxyl-terminal hydrolase isozyme L1 | 791 ± 1828 | 991 ± 676 | 76223 ± 38825 | 0.004 | 0.001 | 0.959 |

Proteins that met the p value<0.01 criteria were filtered for AUC curves>0.9 to determine candidate proteins as "excellent" biomarkers to differentiate culture positive (febrile+afebrile UTI) samples from the combined culture negative samples (CN no pyuria+CNpyuria) with the results presented in FIGS. 1A-1H where areas under the curve (AUC) demonstrated the 8 candidate biomarkers that met p value filtering criteria and had AUC>0.9. FIG. 1A B-cell lymphoma protein, FIG. 1B C-X-C motif chemokine 6, FIG. 1C C-X-C motif chemokine 13, FIG. 1D cathepsin S, FIG. 1E heat shock 70 kDA protein 1A, FIG. 1F mitogen activated protein kinase, FIG. 1G protein E7 HPV18, FIG. 1H transgelin 2

FIGS. 2A-2H show candidate biomarker scatter plot results of urine biomarker to creatinine ratio threshold levels with the highest likelihood ratio (LR) to differentiate UTI (febrile+afebrile) samples from the combined control samples (control negative (CN) no pyuria+control negative (CN) pyuria). Scatter plots of urine biomarkers that met p value and AUC criteria show threshold values that differentiate between UTI and no UTI (CN pyuria and CN no pyuria urine). The CN pyuria and CN no pyuria samples were separated for graphical reasons, but not for determination of the likelihood ratio (LR). Threshold levels and LRs are presented for B-cell lymphoma protein FIG. 2A, C-X-C motif chemokine 6 FIG. 2B, C-X-C motif chemokine 13 FIG. 2C, cathepsin S FIG. 2D, heat shock 70 kDA protein 1A FIG. 2E, mitogen activated protein kinase FIG. 2F, protein E7 HPV18 FIG. 2G, and transgelin 2 FIG. 2H. Biomarker units are relative fluorescent units/ml (RFU) and creatinine units are mg/dl.

Figure 3:
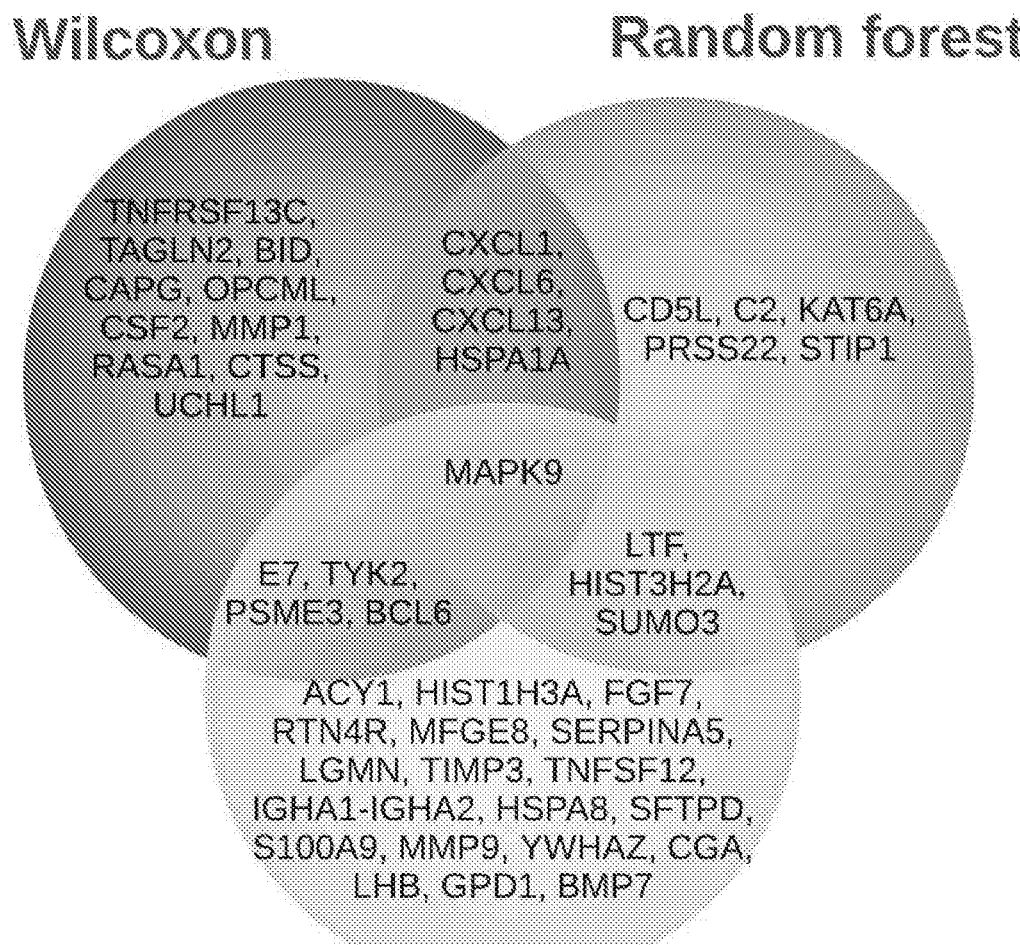
FIG. 3. Summary of the 45 most frequently occurring proteins selected using 3 feature selection methods is provided in Table 3.

FIG. 3 shows the methods of Random forest, ReliefF, and Wilcoxon rank-sum test, as the three feature selection method, applied to determine the best combination of urine protein biomarkers that achieved the best prediction performance. Forty-five (45) most frequently occurring urine proteins were selected during the feature selection process, with 29% overlapping with each other (See Table 3 and FIG. 3).

| Wilcoxon rank-sum test | |
|---|---|
| Target Full Name | Symbol |
| Growth-regulated alpha protein | CXCL1 |
| Cathepsin S | CTSS |
| C-X-C motif chemokine 6 | CXCL6 |
| Heat shock 70 kDa protein 1A | HSPA1A |
| Transgelin-2 | TAGLN2 |
| Protein E7 _HPV18 | E7 |
| Mitogen-activated protein kinase 9 | MAPK9 |
| Ras GTPase-activating protein 1 | RASA1 |
| Granulocyte-macrophage colony-stimulating factor | CSF2 |
| Macrophage-capping protein | CAPG |
| Tumor necrosis factor receptor superfamily mem... | TNFRSF13C |
| B-cell lymphoma 6 protein | BCL6 |
| C-X-C motif chemokine 13 | CXCL13 |
| Opioid-binding protein/cell adhesion molecule | OPCML |
| BH3-interacting domain death agonist | BID |
| Interstitial collagenase | MMP1 |
| Proteasome activator complex subunit 3 | PSME3 |
| Non-receptor tyrosine-protein kinase 2 | TYK2 |
| Ubiquitin carboxyl-terminal hydrolase isozyme L1 | UCHL1 |
| Random forest | |
| Histone H2A type 3 | HIST3H2A |
| Growth-regulated alpha protein | CXCL1 |
| Brain-specific serine protease 4 | PRSS22 |
| Lactotransferrin | LTF |
| Complement C2 | C2 |
| Heat shock 70 kDa protein 1A | HSPA1A |
| C-X-C motif chemokine 13 | CXCL13 |
| C-X-C motif chemokine 6 | CXCL6 |
| Stress-induced-phosphoprotein 1 | STIP1 |
| Small ubiquitin-related modifier 3 | SUMO3 |
| Histone acetyltransferase KAT6A | KAT6A |
| CDS antigen-like | CDSL |
| Mitogen-activated protein kinase 9 | MAPK9 |
| ReliefF | |
| B-cell lymphoma 6 protein | BCL6 |
| Pulmonary surfactant-associated protein D | SFTPD |

-continued

| Wilcoxon rank-sum test | |
| --- | --- |
| Target Full Name | Symbol |
| Plasma serine protease inhibitor | SERPINA5 |
| Heat shock cognate 71 kDa protein | HSPA8 |
| Lactadherin | MFGE8 |
| Bone morphogenetic protein 7 | BMP7 |
| Matrix metalloproteinase-9 | MMP9 |
| Mitogen-activated protein kinase 9 | MAPK9 |
| Protein E7 HPV18 | E7 |
| Histone H2A type 3 | HIST3H2A |
| Lactotransferrin | LTF |
| Immunoglobulin A | IGHA1-IGHA2 |
| 14-3-3 protein zeta/delta | YWHAZ |
| Glycerol -3-phosphate dehydrogenase 1 | GPD1 |
| Tumor necrosis factor ligand superfamily member 12 | TNFSF12 |
| Protein S100-A9 | S100A9 |
| Fibroblast growth factor 7 | FGF7 |
| Histone H3.1 | HIST1H3A |
| Luteinizing hormone | CGA LHB |
| Proteasome activator complex subunit 3 | PSME3 |
| Small ubiquitin-related modifier 3 | SUMO3 |
| Non-receptor tyrosine-protein kinase TYK2 | TYK2 |
| Aminoacylase-1 | ACY1 |
| Reticulon-4 receptor | RTN4R |
| Metalloproteinase inhibitor 3 | TIMP3 |
| Legumain | LGMN |

As shown in the Venn Diagram of FIG. 3, 12 urine protein biomarkers selected by at least two methods were identified and include Mitogen -activating protein kinase 9 (MAPK9), C-X-C motif chemokine 1 (CXCL1), C-X-C motif chemokine 6 (CXCL6), C-X-C motif chemokine 13 (CXCL13), heat shock 70 kDA protein 1A (HSPA1A), protein E7 HPV18 (E7), non-receptor tyrosine-protein kinase (TYK2), proteasome activator complex subunit 3 (PSME3), B-cell lymphoma 6 protein (BCL6), lactotransferrin (LTF), histone H2A type 3 (HIST3H2A) and small ubiquitin-related modifier 3 (SUMO3).

The best AUC score was achieved with the SVM classifier with a radial basis function kernel (AUC score of 0.91) and with the dataset of Random forest algorithm selected urine proteins. FIG. 3 shows the thirteen most frequently occurring proteins identified in feature selection during the 5-fold cross-validation process. Expressions of all these proteins were elevated, with the average expression more than 18 times higher in the UTI group than in the non-UTI group. The expression for heat shock 70 kDa protein 1A (HSPA1A) was detected in UTI group at levels more than 43-fold those detected in non-UTI group.

Figure 4A:
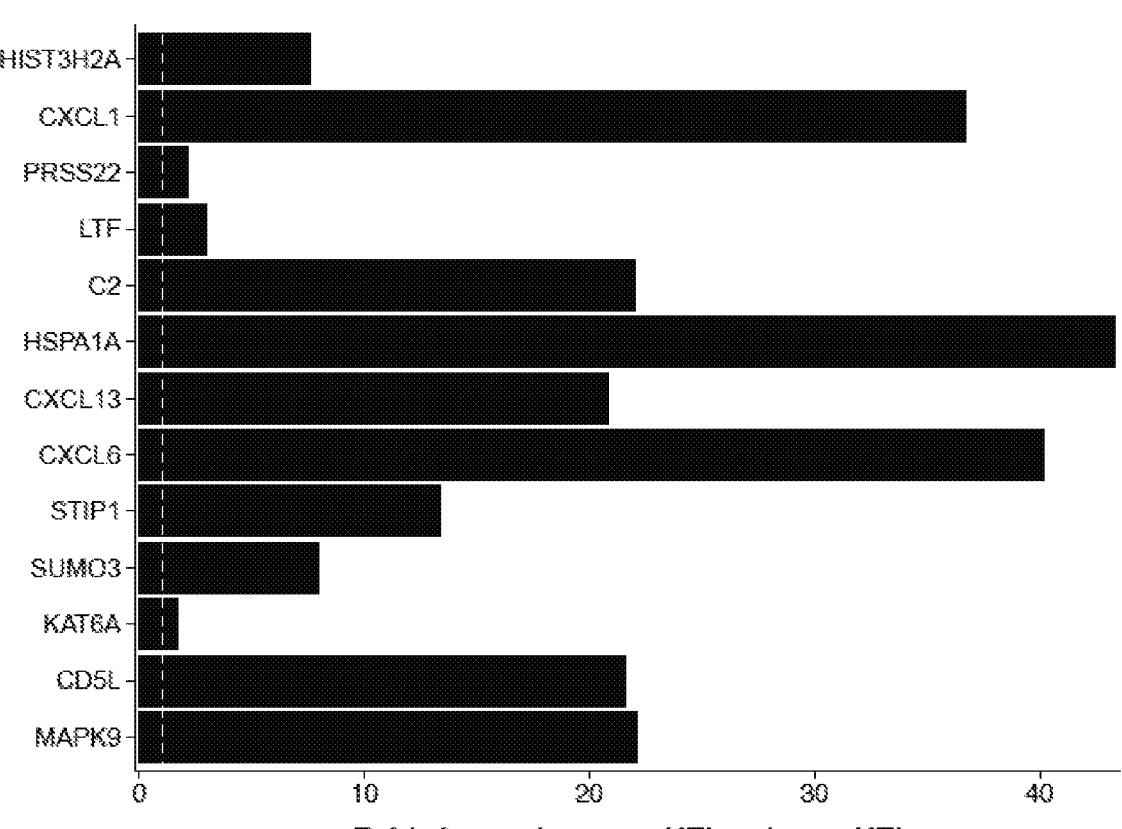
FIG. 4A & 4B.
Figure 4B:
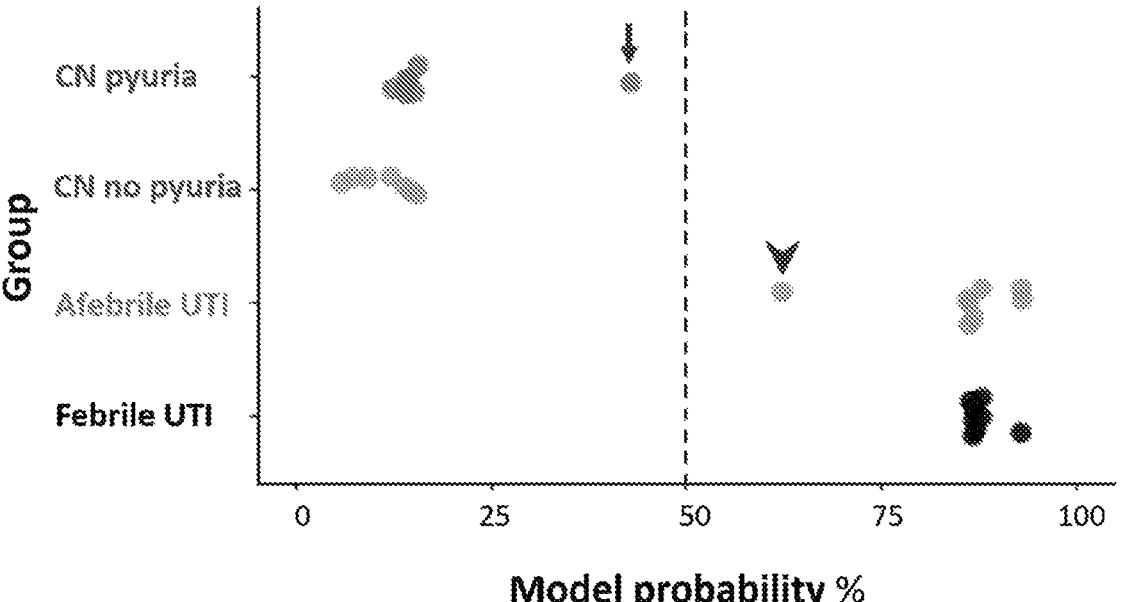
Figure 5:
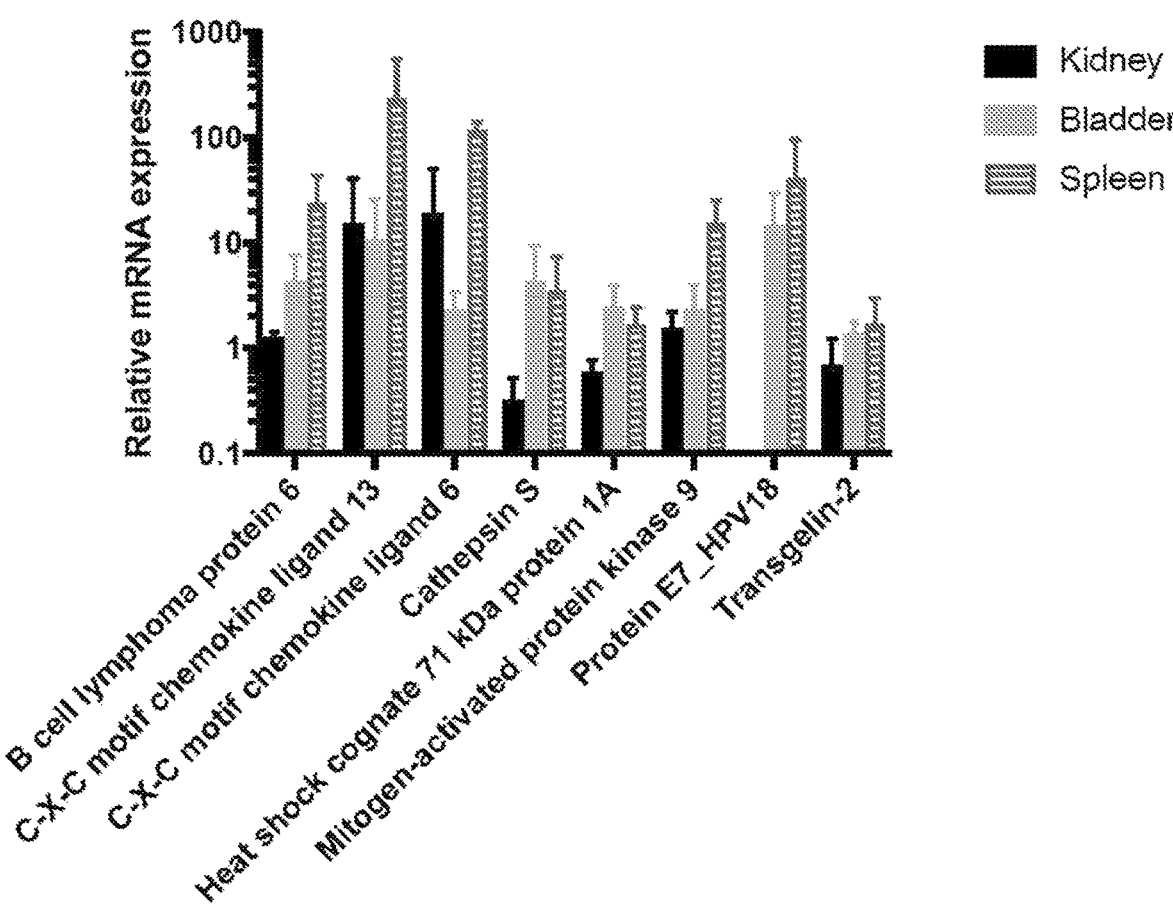
FIG. 5. Relative mRNA expression normalized to GUSB1 was identified in the bladder, kidney and spleen for all candidates that met AUC and p value filtering criteria except for Protein E7 HPV18 in the kidney. Protein E7 HPV18 Ct did meet the threshold for cutoff of 35 in the bladder or spleen, but the melting curves had >1 peak. Bladder and spleen relative mRNA expression generally appeared higher in the bladder and spleen compared to the kidney.

FIGS. 4A & 4B show the UTI class probability estimate calculated based on the SVM decision values for each sample. The dashed black line shows where the 50% probability lies. Generally, model probability of predicting UTI samples was >80%. There are two outliers. One outlier was an 18 year old female with CN pyuria (purple arrow) who presented with left flank pain, fever, and dysuria along with 1+LE on UA and had 43.4% UTI probability. The other outlier was a 3 year old female who presented with fever and abdominal pain, along with 1+LE and had 62.7% UTI probability. The urinary tract expression of the ten leading candidate proteins (FIG. 1) was not well known, human kidney, bladder, and spleen tissue mRNA expression were evaluated by real time polymerase chain reaction (RT PCR), shown in FIG. 5. Specifically, relative mRNA expression normalized to GUSB1 was identified in the bladder, kidney and spleen for all candidates that met AUC and p value filtering criteria except for Protein E7 HPV18 in the kidney. Protein E7 HPV18 Ct did meet the threshold for cutoff of 35 in the bladder or spleen, but the melting curves had>1 peak. Bladder and spleen relative mRNA expression generally appeared higher in the bladder and spleen compared to the kidney.

Protein expression was evaluated using the Human Protein Atlas Renal, if the protein was presented on this resource. Renal tubular, bladder urothelial, and spleen expression was present for all of the evaluated proteins. Kidney, bladder and spleen expression was detected for C-X-C motif chemokine 13, cathepsin S, heat shock 70 k DA protein 1A, mitogen activated protein kinase. Renal tubular expression is present for C-X-C motif chemokine 13, heat shock 70 kDA protein 1A, and mitogen activated protein kinase that appears highest in tubules with appearances consistent with collecting ducts. Cathepsin S expression appears highest in tubules with appearances consistent with proximal tubule cells and bladder expression is generally highest in luminal urothelial cells. Spleen expression is generally strongest in the red pulp cells.

As FIG. 1 shows, eight proteins that were significantly (p<0.01) elevated in UTI samples compared to CN pyuria and CN no pyuria samples with "excellent" biomarker potential were identified and termed candidate biomarker proteins. Few of these proteins had been reported involved in UTI pathophysiology. Some of the proteins that segregated to the UTI group, but with ROC area under the curves of <0.9, shown in Table 2, have previously reported roles in UTI. Pulmonary surfactant-associated protein D (SP-D) inhibits the growth of uropathogenic *E. coli* and regulates renal inflammation via the p38 MAPK related pathway during UTI. Granulocyte colony-stimulating factor (G-CSF) regulates neutrophil migration and suppresses macrophage activation and pro-inflammatory cytokine expression during UTI. SP-D and G-CSF has biological relevance in human UTI.

Some of the candidate proteins shown in FIG. 1 have been associated with bacterial interactions with mucosal surfaces other than the urinary tract. Cathepsin S (CTSS) expression is upregulated during periodontal infections. Transgelin 2 mimics bacterial SipA, a protein that promotes bacterial entry into cells, and promotes phagocytosis in lipopolysaccharide activated macrophages. C-X-C motif chemokine 13 is required for recruitment of specialized B cells, antibody production and the bacterial defense of the peritoneal and pleural cavities. The involvement of cathepsin S, transgelin 2 and C-X-C motif chemokine 13 with other infections provides a foundation for the evaluation of the potential role of these proteins in UTI pathophysiology.

No studies known have associated B cell lymphoma protein 6, heat shock 70 kDA protein 1A, mitogen activated protein kinase 9 or Protein E7 HPV 18 with UTI or other bacterial infections. B cell lymphoma protein 6 was initially described for its regulation of lymphocyte growth and development, but has been demonstrated to function as a checkpoint regarding the initiation of the innate immune response to cystosolic RNA viruses. Heat shock 70 kDA protein 1A is induced by oxidative stress. Because UTI results in oxidative stress and leads to insufficiency of endogenous antioxidants, heat shock 70 kDA protein 1A conceptually has a role during UTI but its association has never been evaluated. Mitogen protein kinase 9 and Protein E7 HPV 18 are involved in innate response to viral infections. Although they have not been well studied in the role of UTI or other bacterial infections, elevated urine levels of B cell lymphoma protein 6, heat shock 70 kDA protein 1A, mitogen activated protein kinase 9, and protein E7 HPV 18 during UTI may demonstrate their involvement with bacterial innate immunity. Human virome studies have had variable results regarding increased Protein E7 HPV18 expression during UTI. HPV18 is included in the vaccine for this virus, however 24/32 (75%) of included patients were <11 years of age, younger than the recommend age for the HPV vaccine. Protein E7 HPV 18 may represent a virus with homologous regions such as adenovirus E1a. Mitogen activated protein 5, along with C-X-C chemokine ligand 13 and heat shock protein expression has been detected in the spleen, bladder lumen, and collecting duct of the kidney; the renal collecting duct, the initial kidney tubular section encountered by ascending uropathogens, is known to have innate immune functions.

Somalogic proteomics data were used to construct a machine learning predictive model for urinary tract infection; support vector machine classifier was applied in solving the classification problem on proteomics data. A nested cross-validation approach that performed hyperparameter tuning and model optimization in the inner cross-validation loop was adopted to obtain an unbiased performance estimation. Optimal models were evaluated independently in the outer cross-validation loop. This avoided the optimistic bias introduced into the performance estimate due to the use of the same cross-validation procedure for both hyperparameter optimization and performance evaluation. The SVM model had a slightly lower AUC than some of the individual proteins, which was likely because results for the SVM model were divided into a test and validation cohort. The SVM model will likely outperform single biomarkers with more samples, and may be more accurate than urine culture. The patient assigned to the culture negative pyuria, with a UTI probability score of 43.4%, shown in FIG. 4, presented with left flank pain, fever, dysuria and UTI history; the patient might have had an actual UTI with an organism that did not grow on culture. Enhanced urine culture and sequencing may determine if these actually represent culture negative UTI.

Discussion

A nonbiased proteomic methodology was used to identify a protein profile that differentiates UTI from CN no pyuria along with CN pyuria samples. We identified 8 proteins that were significantly (p<0.01) elevated in UTI samples compared to CN pyuria and CN no pyuria samples with "excellent" biomarker potential (see FIG. 1A-1H). Very few of these proteins have been reported involved in UTI pathophysiology. Some of the proteins that segregated to the UTI group, but with ROC area under the curves of <0.9 (Table 2) have previously reported roles in UTI. Applicant.

After an extensive search of the literature we were unable to identify prior studies associating B cell lymphoma protein 6, heat shock 70 kDA protein 1A, mitogen activated protein kinase 9 or Protein E7 HPV 18 with UTIs or other bacterial infections. B cell lymphoma protein 6, was initially described for its regulation of lymphocyte growth and development, but has been demonstrated to function as a checkpoint regarding the initiation of the innate immune response to cystosolic RNA viruses. heat shock 70 kDA protein 1A is induced by oxidative stress. Because UTIs result in oxidative stress and lead to insufficiency of endogenous antioxidants, therefore heat shock 70 kDA protein 1A conceptually has a role during UTI, but to our knowledge, this association has never been evaluated. Mitogen protein kinase 9 and Protein E7 HPV 18 are involved in innate response to viral infections. Although they have not been well studied in the role of UTIs or other bacterial infections, elevated urine levels of B cell lymphoma protein 6, heat shock 70 kDA protein 1A, mitogen activated protein kinase 9 and protein E7 HPV 18 during UTI raises the possibility that these proteins are involved with bacterial innate immunity. Past studies of the human virome, have had variable results regarding increased Protein E7 HPV18 expression during UTI. HPV18 is included in the vaccine for this virus, however 24/32 (75%) of included patients were <11 years of age, younger than the recommend age for the HPV vaccine. It is possible that Protein E7 HPV 18 represents a virus with homologous regions such as adenovirus E1 a. We demonstrated mitogen activated protein 5, along with C-X-C chemokine ligand 13 and heat shock protein expression was identified in the spleen, bladder lumen and collecting duct of the kidney. We have previously demonstrated that the renal collecting duct, the initial kidney tubular section encountered by ascending uropathogens has innate immune functions.

To the best of our knowledge, this is the first study that uses Somalogic proteomics data to construct a machine learning predictive model for urinary tract infection. In this study, we explored the application of support vector machine classifier in solving the classification problem on proteomics data. In order to obtain an unbiased performance estimation, we have adopted a nested cross-validation approach that performing hyperparameter tuning and model optimization in the inner cross-validation loop and evaluated the optimal models independently in the outer cross-validation loop. This design avoids the optimistic bias introduced into the performance estimate due to the use of the same cross-validation procedure for both hyperparameter optimization and performance evaluation. Our SVM model had a slightly lower AUC than some of the individual proteins. This is likely because for the SVM model we divided our results into a test and validation cohort. We anticipate that the SVM model will outperform single biomarkers in future studies with many more samples. It is also possible that our SVM model may be more accurate than urine culture. The patient assigned to the CN pyuria with a UTI probability of score of 43.4% (FIG. 4B) presented with left flank pain, fever, dysuria and UTI history; we speculate that they might have had an actual UTI with an organism that did not grow on culture. In the future, enhanced urine culture and sequencing could be applied to similar samples to help determine if these actually represent culture negative UTIs.

The invention claimed is:

1. A method for treating a patient having a urinary tract infection, said method comprising the steps of identifying said patient having a urinary infection wherein said identification step comprises obtaining a urine sample from said patient;

analyzing said urine sample for the presence of each of the proteins that have at least 95% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPAIA; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31); wherein the presence of said one or more proteins identified a patient with a urinary tract infection;

obtaining a reference level of each of the proteins having at least 95% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31);

determining the concentration of the corresponding proteins having at least 95% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPAIA; SEQ ID NO: 26), mitogen activated protein kinase 9 (MAPK9; SEQ ID NO: 25), protein E7 HPV18 (Eb7; SEQ ID NO: 30), and transgelin-2 (TAGLN2; SEQ ID NO: 31) in said urine sample, wherein the concentration of each of said proteins in said urinary sample is determined and compared to said reference levels wherein a detected higher level of each of said proteins in said urine sample relative to the corresponding reference levels indicates the patient has a urinary tract infection; and treating said identified patient with antibiotics.

2. The method of claim 1 wherein the proteins in the sample are identified by an enzyme linked immunosorbent assay (ELISA).

3. The method of claim 1 wherein the proteins in the sample are identified by mass spectroscopy.

4. A method of treating a urinary tract infection in a patient, said method comprising:

receiving an identification of the patient as having a protein profile present in a urine sample obtained from said patient, wherein the protein profile comprises five or more proteins that have at least 95% sequence identity to a protein selected from the group consisting of B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPA1A; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31); and treating said identified patient with antibiotics.

5. A method for treating a patient having a urinary tract infection, said method comprising the steps of identifying said patient having a urinary infection wherein said identification step comprises obtaining a urine sample from said patient;

measuring in the urine sample of the patient each of proteins B-cell lymphoma 6 protein (BCL6; SEQ ID NO: 23), C-X-C motif chemokine 6 (CXCL6), C-X-C motif chemokine 13 (CXCL13; SEQ ID NO: 29), cathepsin S (CTSS; SEQ ID NO: 24), heat shock 70 kDA protein 1A (HSPAIA; SEQ ID NO: 26), mitogen activated protein kinase 9 (MAPK9; SEQ ID NO: 25), protein E7 HPV18 (E7; SEQ ID NO: 30), and transgelin-2 (TAGLN2; SEQ ID NO: 31); and normalizing the concentration of each protein to creatinine, to account for the concentration of the patient's urine sample to obtain a normalized patient sample;

diagnosing a urinary tract infection if the protein to creatinine ratio result exceeds a threshold value, and treating said identified patient with antibiotics.

6. The method of claim 5 wherein the measuring steps are performed at a point of care.

7. The method of claim 5 where a likelihood ratio diagnoses the patient with a urinary tract infection, versus culture negative pyuria, versus culture negative no pyuria.

* * * * *